United States Patent
Thetford et al.

(10) Patent No.: US 9,540,486 B2
(45) Date of Patent: *Jan. 10, 2017

(54) AROMATIC DISPERSANT COMPOSITION

(71) Applicant: Lubrizol Advanced Materials, Inc., Cleveland, OH (US)

(72) Inventors: Dean Thetford, Norden (GB); Andrew J. Shooter, Wilmslow (GB); Stuart N. Richards, Frodsham (GB)

(73) Assignee: Lubrizol Advanced Materials, Inc., Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/397,203

(22) PCT Filed: Apr. 25, 2013

(86) PCT No.: PCT/US2013/038114
§ 371 (c)(1),
(2) Date: Oct. 27, 2014

(87) PCT Pub. No.: WO2013/165792
PCT Pub. Date: Nov. 7, 2013

(65) Prior Publication Data
US 2015/0148476 A1    May 28, 2015

Related U.S. Application Data

(60) Provisional application No. 61/641,342, filed on May 2, 2012.

(51) Int. Cl.
| | | |
|---|---|---|
| C08G 69/48 | (2006.01) |
| C08G 63/91 | (2006.01) |
| C08F 10/00 | (2006.01) |
| C08L 77/00 | (2006.01) |
| C08L 67/00 | (2006.01) |
| C08L 23/36 | (2006.01) |
| C08L 77/12 | (2006.01) |
| C09D 123/36 | (2006.01) |
| C09D 167/00 | (2006.01) |
| C09D 177/00 | (2006.01) |
| C09D 177/12 | (2006.01) |
| A61K 31/4745 | (2006.01) |
| C09B 67/46 | (2006.01) |
| C08G 65/333 | (2006.01) |
| C08G 59/22 | (2006.01) |
| C08G 59/50 | (2006.01) |
| C08G 65/332 | (2006.01) |
| C08L 63/00 | (2006.01) |
| C08F 222/10 | (2006.01) |
| C08J 7/04 | (2006.01) |

(52) U.S. Cl.
CPC ........... *C08G 69/48* (2013.01); *A61K 31/4745* (2013.01); *C08F 10/00* (2013.01); *C08G 59/22* (2013.01); *C08G 59/504* (2013.01); *C08G 63/91* (2013.01); *C08G 65/3326* (2013.01); *C08G 65/33341* (2013.01); *C08L 23/36* (2013.01); *C08L 63/00* (2013.01); *C08L 67/00* (2013.01); *C08L 77/00* (2013.01); *C08L 77/12* (2013.01); *C09B 67/0089* (2013.01); *C09D 123/36* (2013.01); *C09D 167/00* (2013.01); *C09D 177/00* (2013.01); *C09D 177/12* (2013.01); *C08F 222/1006* (2013.01); *C08G 2650/32* (2013.01); *C08G 2650/50* (2013.01); *C08J 7/04* (2013.01); *Y10S 524/923* (2013.01)

(58) Field of Classification Search
CPC ..... C08J 7/04; C09B 67/0089; Y10S 524/923; C08F 222/1006; A61K 31/4745
See application file for complete search history.

(56) References Cited

U.S. PATENT DOCUMENTS

| | | |
|---|---|---|
| 5,688,312 A | 11/1997 | Sacripante et al. |
| 6,440,207 B1 | 8/2002 | Schulz et al. |
| 7,265,197 B2 | 9/2007 | Huber et al. |
| 2005/0120911 A1 | 6/2005 | Huber et al. |
| 2007/0221913 A1 | 9/2007 | Lee et al. |
| 2010/0130678 A1* | 5/2010 | Richards .......... C08F 8/30 524/608 |

FOREIGN PATENT DOCUMENTS

| | | |
|---|---|---|
| EP | 2199312 A1 | 6/2010 |
| WO | 2007139980 A2 | 12/2007 |
| WO | 2008028954 A2 | 3/2008 |

* cited by examiner

*Primary Examiner* — Gregory Listvoyb
(74) *Attorney, Agent, or Firm* — Samuel B. Laferty, Esq.; Teresan W. Gilbert, Esq.

(57) ABSTRACT

The present invention relates to a composition containing a particulate solid, a polar or non-polar organic medium, and a polymer chain having at least one fused aromatic imide pendant group. The invention further provides compositions for coatings, inks, toners, plastic materials (such as thermoplastics), plasticizers, plastisols, crude grinding and flush.

13 Claims, No Drawings

AROMATIC DISPERSANT COMPOSITION

FIELD OF INVENTION

The present invention relates to a composition containing a particulate solid, a polar or non-polar organic medium, and a polymer chain having at least one fused aromatic imide pendant group. The invention further provides compositions for coatings, inks, toners, plastic materials (such as thermoplastics), plasticisers, plastisols, crude grinding and flush.

BACKGROUND OF THE INVENTION

Many formulations such as inks, paints, millbases and plastics materials require effective dispersants for uniformly distributing a particulate solid in a polar organic medium or a non-polar organic medium. For inks, it is desirable for ink manufacturers to generate printed products of high resolution and quality. The adaptability of printing process to cater for the ever widening range of base substrates, resins and pigments is a challenge. The pigment dispersion should be compatible with the different formulations used to ensure good adhesion and resistance of the final coating. Poor pigment dispersion or stabilisation can result in agglomeration or settling within the polar organic liquid medium or a non-polar organic liquid medium (e.g., ink or coating) lowering the gloss and aesthetic appeal.

U.S. Pat. No. 7,265,197 discloses dispersing pigments in ink compositions with a dispersant having formula:

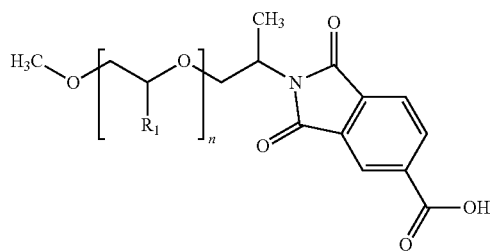

where $R_1$ is individually selected from the group consisting of H and $CH_3$, and n is an integer from 4 to 400).

International publication WO 2008/028954 discloses imide dispersant compounds containing terminal acidic groups in both a polar and a non-polar organic medium, where the dispersant compound is represented by the structure

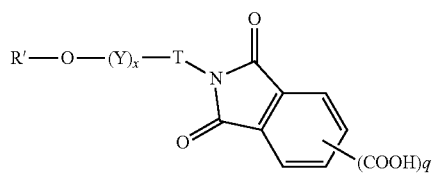

where T is $-(CH_2)_3-$ or $-CH_2CH(CH_3)-$; R' is H or $C_{1-50}$-optionally substituted hydrocarbyl group, or $C_{1-50}$-optionally substituted hydrocarbonyl; Y is $C_{2-4}$-alkyleneoxy; x is 2 to 90; and q is 1 or 2, with the proviso that in Formula (1a), when q is 1, T is $-(CH_2)_3-$, and when q is 2, T is $-(CH_2)_3-$ or $-CH_2CH(CH_3)-$ U.S. Pat. No. 5,688,312 discloses an ink composition comprised of a colourant and an imide or bisimide with a viscosity of from about 1 centipoise to about 10 centipoise at a temperature of from about 125 to about 180° C. The imide or bisimide may be prepared by reacting phthalic anhydride and a mono- or diamine. The monoamine may be for example dodecylamine, or stearylamine. The diamine may be 1,12-dodecanediamine.

International Patent Application WO 2007/139980 discloses a reaction product of at least one di-anhydride with at least two reactants which are different from each other, each of which reactants contains a primary or secondary amino, hydroxyl or thiol functional group, and at least one of which reactants is polymeric. The reaction product is useful in compositions such as inks and coatings.

U.S. Pat. No. 6,440,207 discloses a process for preparing dispersible dry organic pigments for aqueous systems by (a) milling a mixture containing (1) one or more organic pigments, (2) at least about 1% by weight, relative to the organic pigment, of one or more aromatic polyalkylene oxide dispersants, (3) 0 to about 10 parts by weight, relative to the organic pigment, of a milling liquid in which the organic pigment is substantially insoluble, (4) 0 to about 50% by weight, relative to the organic pigment, of one or more milling additives other than dispersant (2), and (5) 0 to about 20% by weight, relative to the organic pigment, of one or more surface treatment additives; (b) optionally, adding to the milled pigment (6) one or more liquids in which the organic pigment is substantially insoluble in amounts such that the total solids content is not reduced below about 10%, and (7) one or more multivalent metal salts and/or one or more quaternary ammonium salt; and (c) isolating the milled organic pigment. The aromatic polyalkylene oxide dispersant may be prepared by reacting in an autoclave containing 250 g of deionized water 19.8 (0.100 mol) of 1,8-naphthalic anhydride and 105 (0.105 mol) of Jeffamine™ XTJ-506 (83 wt % ethylene oxide, 17 wt % propylene oxide). The autoclave was sealed, heated with stirring to 150° C., and maintained at 150° C. for five hours. After the reaction had cooled, the resultant brown liquid was discharged into a beaker to which was then added 15 g of decolourizing charcoal. After stirring overnight, the suspension was filtered and the filter cake washed with water, yielding approximately 500 g of an amber-coloured filtrate having a 23.63% solids content. The dry pigment can be employed in water-based paint systems.

SUMMARY OF THE INVENTION

One objective of the present invention is to provide compounds that are capable of at least one of improving colour strength, other tinctorial properties, increasing a particulate solid load, forming improved dispersions, having improved brightness, producing a composition with reduced viscosity, maintain stable dispersion, reduced particle size and reduced particle size distribution (typically reduced to an average of 150 nm or less, for example in the range of 70-135 nm), reduced haze, improved gloss, and increased jetness (especially when the composition is black). The composition of the present invention may also be stable under ambient storage, and high temperature storage conditions.

Electron withdrawing groups are well known to a person skilled in the art of organic synthesis. Examples of electron withdrawing groups include but are not limited to a halogen (such as —Cl, —Br, or —F), a nitrile, a carbonyl group, a nitro group, a sulphamoyl group, a sulphonate group, a hydroxy group, or an amino group.

The electron withdrawing group may be either an activating group or a deactivating group.

The activating group may include a hydroxy group, an amino group, or a halogen. Typically, the activating group may include halogen such as —Cl.

The deactivating group may include a nitrile, a carbonyl group, a carboxyl group, a nitro group, a sulphamoyl group, or a sulphonate group. Typically, the deactivating group may include a nitro group, a carboxyl group or a sulphonate group.

Typically, the electron withdrawing group may be deactivating group.

In one embodiment, the invention provides a polymer comprising a polymer chain having at least one fused aromatic imide pendant group, wherein the polymer may be represented by formula (1):

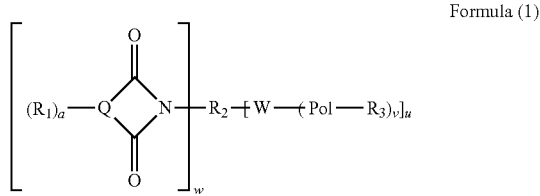

Formula (1)

wherein each variable may independently be
$R_1$ may be a substituent on Q ring in any position available for bonding to a substituent group and $R_1$ may be independently represented by one or more of —H, or an electron withdrawing group (such as —$NO_2$, —$SO_2NR'_2$, —C(O)R', —$SO_3M$, —C(O)OM, halo e.g., —Cl or —Br, —$NH_2$, or —OR'), or an electron releasing group (such as an alkyl group e.g., —$CH_3$), (typically when $R_1$ may be other than —H, the number of non-H groups defined by a may be 0 to 2, 0 to 1, 0, or 1). For example, $R_1$ may be —H, —$CH_3$, —Cl, —$NO_2$, —$SO_3M$, or —C(O)OM, —CN (typically when a may be non-zero $R_1$ may be —Cl, —$SO_3M$ or —$NO_2$);

M may be H, a metal cation, —$NR'_4^+$, or mixtures thereof;
R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbylene group or a $C_1$ to $C_{20}$, or $C_1$ to $C_{12}$, or $C_1$ to $C_6$ hydrocarbonylene group (when $R_2$ contains more than 2 carbon atoms, the hydrocarbylene group or hydrocarbonylene group may be linear or branched) or mixtures thereof;

$R_3$ may be H or $C_{1-50}$ (or $C_{1-20}$)-optionally substituted hydrocarbyl group that bonds to a terminal oxygen atom of the polymer chain forming a terminal ether or terminal ester group and may or may not contain a group capable of polymerization such as a vinyl group, or $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof;

Pol may be a homopolymer chain or a copolymer chain, wherein the polymer chain may be selected from the group consisting essentially of a Poly(ether), Poly(ester), Poly (ester amide), Poly(alkylene), Poly(amide) or mixtures thereof;

u may be 1 to 3 or 1 to 2, or 1;
v may be 1 to 2;
w may be 1 to 3 or 1 to 2, or 1;
v=1 when W=Oxygen, Sulphur, or >NG;
G may be hydrogen or a hydrocarbyl group containing 1 to 200, or 1 to 100, or 1 to 30 carbon atoms;
v=2 when W=nitrogen; and
Q may be a fused aromatic ring containing 4n+2 π-electrons, wherein n=2 or more, typically 2 to 5, or 2 to 4, or 2 to 3, or 2), and Q may be bonded to the imide group in such a way to form a 5 or 6 membered imide ring (typically 6 membered).

In one embodiment, Pol may be selected from Poly (ether), Poly(ester) and mixtures thereof.

In one embodiment, the polymer of the present invention (typically represented by formula (1)) may be obtained/obtainable by a process comprising reacting an amine ended polymer with a fused aromatic di-acid or anhydride or other acid-forming derivative (such as di-ester, di-amide, di-acid dichloride) to form a fused aromatic imide with a polymer chain. The reaction to form the imide may be carried out at a sufficiently high temperature known to the skilled person to favour imide formation e.g., at least 100° C., or 150° C. to 200° C.

In one embodiment, the polymer of the present invention (typically represented by formula (1)) may be obtained/obtainable by a process comprising:

Step (1): reacting (i) amino acid or (ii) an aminoalcohol, or (iii) an aminothiol, or (iv) a diamine or polyamine,
with a fused aromatic di-acid or anhydride or other acid-forming derivative (such as di-ester, di-amide, di-acid dichloride) to form an acid-functionalised fused aromatic imide or a hydroxyl-functionalised fused aromatic imide, or a thiol-functionalised fused aromatic imide, or an amino-functionalised fused aromatic imide respectively. The first step of the reaction (to form the imide) may be carried out at a sufficiently high temperature known to the skilled person to favour imide formation e.g., at least 100° C., or 150° C. to 200° C.;

Step (2): reacting the acid-functionalised fused aromatic imide or the hydroxyl-functionalised fused aromatic imide, or the thiol-functionalised fused aromatic imide, or the amino-functionalised fused aromatic imide with a polymer chain, or monomers that polymerise to form the polymer chain.

The product of Step (1) may be used as a polymerization terminating agent if the polymer chain has been pre-formed before reaction in Step (2).

The product of Step (1) may be used as a polymerization initiator if the polymer chain may be grown from one or more monomers in Step (2).

When the product of Step (1) may be further reacted in an alkoxylation reaction, the reaction temperature may be 100° C. to 200° C. in the presence of a base catalyst such as potassium hydroxide or sodium hydroxide.

When the product of Step (1) or Step (2) may be further reacted in an esterification reaction, the reaction temperature may be 50° C. to 250° C. or 150° C. to 200° C., optionally in the presence of an esterification catalyst.

The esterification catalyst may be any previously known to the art and include tin(II) octanoate, tetra-alkyl titanate, for example, tetrabutyltitanate, zinc salt of an organic acid, for example, zinc acetate, zirconium salt of an aliphatic alcohol, for example, zirconium isopropoxide, toluene sulphonic acid or a strong organic acid such as trifluoroacetic acid, or phosphoric acid.

The polymer of formula (1) may be capped with a $R_3$ group. The $R_3$ group may be derived from a carboxylic acid, an acid derivative, an alcohol, a thiol, an amine, or an isocyanate. The acid, acid derivative, alcohol, thiol and amine are described herein below. The reaction conditions for capping the polymer chain to result in the polymer of the present invention with an acid, acid derivative, alcohol, an amine or an isocyanate are reactions known in the art.

The process may be carried out in an inert atmosphere provided by any inert gas of the Periodic Table but typically nitrogen.

In one embodiment, the invention provides a composition comprising a particulate solid, a non-polar organic medium, and a polymer chain having at least one fused aromatic imide pendant group, wherein the polymer may be represented by formula (1) defined above. The composition may be a millbase, paint or ink.

In one embodiment, the invention provides a composition comprising a particulate solid, a polar organic medium, and a polymer chain having at least one fused aromatic imide pendant group, wherein the polymer may be represented by formula (1) defined above. The composition may be a millbase, paint or ink.

In one embodiment, the invention provides a composition comprising a particulate solid, a non-polar organic medium, and a polymer chain having at least one fused aromatic imide pendant group, wherein the polymer may be represented by formula (1) defined above further comprises a binder. In one embodiment the binder may be nitrocellulose, polyepoxide, polyurethane, alkyd, poly(meth)acrylate, polyester, or polyamide.

In one embodiment, the invention provides a composition comprising a particulate solid, a polar organic medium, and a polymer having at least one fused aromatic imide pendant group, wherein the polymer may be represented by formula (1) defined above further comprises a binder. In one embodiment, the binder may be nitrocellulose, polyurethane, poly(meth)acrylate, polyester, or polyamide.

The present invention also provides a composition comprising a particulate solid (typically a pigment or filler), a non-polar organic medium and a polymer having at least one fused aromatic imide pendant group, wherein the polymer may be represented by formula (1) defined above. The composition may be a millbase, paint or ink.

The present invention also provides a composition comprising a particulate solid (typically a pigment or filler), a polar organic medium and a polymer chain having at least one fused aromatic imide pendant group, wherein the polymer may be represented by formula (1) defined above. The composition may be a millbase, paint or ink.

The particulate solid disclosed herein in a composition of the present invention may be a pigment or a filler. The pigment may in one embodiment be an organic pigment.

The non-polar organic medium may for instance include a mineral oil, an aliphatic hydrocarbon, an aromatic hydrocarbon, a plastic material (typically a thermoplastic resin or a thermoset resin), or a plasticiser.

The polar organic medium may for instance include a ketone, an ester, a glycol ether and ester, or an alcohol.

In one embodiment the invention also provides for a polymer comprising a polymer chain having at least one fused aromatic imide pendant group, wherein the chain may be prepared directly by reacting a fused aromatic di-acid or anhydride with one or more of a polyalkyleneamine (obtained/obtainable from an olefin polymer and an amine). The polymer may also be used in place of the polymer represented by formula (1) in the compositions disclosed herein.

In one embodiment, the invention provides a paint or ink comprising a particulate solid, a non-polar organic medium, a film-forming resin and a polymer of the invention disclosed herein.

In one embodiment, the invention provides a paint or ink comprising a particulate solid, a polar organic medium, a film-forming resin and a polymer of the invention disclosed herein.

The ink may be an ink-jet ink, a flexo ink, a gravure ink, or an offset ink. The ink may be a radiation curable ink.

In one embodiment, the compositions disclosed herein further include a binder.

In one embodiment, the invention provides for a composition comprising a polymer chain having at least one fused aromatic imide pendant group, wherein the polymer may be represented by formula (1) defined above, an organic pigment, and a binder. The binder may be selected from the group consisting of nitrocellulose, polyurethane and polyamide. The composition may be used in an ink for a printing process, such as a flexographic printing process or ink jet inks such as radiation curable, non-impact and drop on demand.

In one embodiment, the invention provides for a composition comprising a polymer chain having at least one fused aromatic imide pendant group, wherein the polymer may be represented by formula (1) defined above, carbon black, and a binder. The binder may be selected from the group consisting of nitrocellulose, polyurethane and polyamide. The composition may be used in an ink for a printing process, such as a flexographic printing process.

In one embodiment, the invention provides a composition comprising a polymer chain having at least one fused aromatic imide pendant group, wherein the polymer may be represented by formula (1) defined above, a particulate solid (typically a pigment or filler), and either (i) a polar organic medium or (ii) a non-polar organic medium, wherein the organic medium may be a plastics material. The plastic material may be a thermoplastic resin or a thermoset resin.

The polymer of the present invention may be present in a composition disclosed herein in an amount ranging from 0.1 wt % to 79.6 wt %, 0.5 wt % to 30 wt %, or 1 wt % to 25 wt % of the composition.

In one embodiment, the invention provides for the use of the polymer chain having at least one fused aromatic imide pendant group, wherein the polymer may be represented by formula (1) defined above as a dispersant in a composition disclosed herein.

In one embodiment, the invention provides for the use of a polymer chain having at least one fused aromatic imide pendant group, wherein the polymer may be represented by formula (1) defined above as a dispersant in an ink composition. The ink composition may have at least one of reduced particle size and reduced particle size distribution (typically reduced to an average of 150 nm or less), reduced haze, improved gloss, and increased jetness (especially when the composition may be black) and be stable under ambient storage, and high temperature storage conditions.

Without being bound by theory, it may be believed that the fused aromatic imide pendant group may act as an anchor group between the polymer of invention and a particulate solid such as a pigment.

DETAILED DESCRIPTION OF THE INVENTION

The present invention provides a composition and use disclosed herein above.

The polymer chain (Pol) may have number average molecular weight of 100 to 10,000, or 100 to 5000, or 300 to 3000, or 400 to 2500.

The number average molecular weight may be determined for a pre-prepared polymer chain by GPC analysis. The number average molecular weight of a polymer that is prepared in-situ i.e., the polymer chain is grown off the imide group may be calculated by determining the degree of polymerisation (DP) which is proportional to the ratio of monomer [M] and initiator [I] (the initiator being the fused aromatic anhydride), and calculated by the formula DP=[M]/[I]. Nuclear magnetic resonance (NMR) can be used to determine the degree of polymerization and thus to calculate number average molecular weight of the polymeric group or polymer segment of the molecule.

Examples of a hydrocarbylene group defined by $R^2$ may include methylene, ethylene, propylene, butylene, pentylene, hexylene, octylene, decylene, dodecylene or their branched isomers. In one embodiment, hydrocarbylene group defined by $R^2$ may be $(-CH_2-)_3$ or $-CH_2CH(CH_3)-$ or $-CH_2CH_2-$.

$R^2$ may be derived from an aminoalcohol, an aminothiol, an aminocarboxylic acid, or an amine having 1 to 3, or 1 to 2, or 1-$NH_2$ group. The amino group may or may not contain additional alkyl groups.

Examples of a diamine include 1,2-diaminoethane, propane-1,3-diamine, butane-1,4-diamine, pentane-1,5-diamine, hexane-1,6-diamine, dodecane-1,12-diamine or mixtures thereof.

Examples of polyamines include N-(2-aminoethyl) 1,3-propane diamine, 3,3'iminobispropylamine, spermidine, bis(hexamethylene)triamine, triethylene triamine, N,N'-bis(3-aminopropyl)-1,3-ethylenediamine, N,N'-bis(2-aminoethyl)-1,3-propanediamine, spermine, tris(2-aminoethyl)amine, tetraethylenepentamine, triethylene tetramine, or diethylene triamine, or mixtures thereof.

The aminoalcohol may be a $C_{2-20}$-aminoalcohol and may or may not contain more than one hydroxyl group and may or may not contain more than one amino group. The aminoalcohol may be ethanolamine, 3-amino-1-propanol, 4-aminobutanol, 2-aminobutanol, 2-amino-2-methyl-1-propanol, 5-amino-1-pentanol, 5-amino-2-pentanol, 2-amino-3-methyl-1-butanol, 6-amino-1-hexanol, 2-amino-1-hexanol, serinol, 4-amino cyclohexanol, 2-(2-aminoethoxyl)ethanol, 3-amino-1,2-propanediol, 2-amino-2-ethyl-1,3-propanediol, tris-(hydroxymethyl)amino methane, tris-(hydroxypropyl) amino methane, 1,3-diamino-2-hydroxy propane, or mixtures thereof.

The amino thiol may be a $C_{2-20}$-aminothiol and may or may not contain more than one thiol group and may or may not contain more than one amino group. The aminothiol may include 2-aminoethanethiol, 3-aminopropane-1-thiol, 4-aminobutane-1-thiol, 5-aminopentane-1-thiol, 6-aminohexane-1-thiol or mixtures thereof.

As used herein the term "hydrocarbonylene group" is a hydrocarbylene group containing a carbonyl group. Typically, a hydrocarbonylene group defined by $R^2$ may include $-(CH_2)_5-C(O)-$, $-(CH_2)_4-C(O)-$, $-(CH_2)_3-C(O)-$, or $-(CH_2)_2-C(O)-$.

The aminocarboxylic acid (or amino-acid) may be an amino-$C_{2-20}$-alk(en)ylene carboxylic acid and may or may not contain more than one carboxylic acid group and may or may not contain more than one amino group. The aminocarboxylic acid may or may not contain other groups containing heteroatoms such as hydroxyl or thiol groups. The alk(en)ylene group may be linear or branched. The alk(en)ylene group of the amino carboxylic acid contains not greater than 12 carbon atoms. Specific examples include 11-amino undecanoic acid, 12-amino dodecanoic acid, 6-amino caproic acid, 4-aminobutyric acid, aspartic acid, glutamic acid, lysine, asparagine, glutamine, threonine, serine, cysteine, β-alanine, glycine, and sarcosine. Mixtures of amino carboxylic acids may be used.

As used herein reference to hydrocarbylene or hydrocarbonylene groups may be linear or branched, and saturated or unsaturated.

The technical feature defined within Q of 4n+2 π-electrons is well known to a skilled person as Hückel's rule. Typically, n may be equal to 2 (i.e., the number of π-electrons is 10), or 3 (i.e., the number of π-electrons is 14). In one embodiment, n may be equal to 2.

Q may be based on naphthalene, an anthracene, a phenanthrene, or mixtures thereof. In one embodiment, Q may be based on naphthalene.

When Q is based on naphthalene, the polymer chain of formula (1) may have a naphthalene imide group such as a 1,2-naphthalene imide, 2,3-naphthalene imide, or a 1,8-naphthalene imide group, or mixtures thereof.

When Q is based on anthracene, the polymer chain of formula (1) may have a 1,2-anthracene imide, 2,3-anthracene imide, or a 1,9-anthracene imide group, or mixtures thereof.

When Q is based on phenanthrene, the polymer chain of formula (1) may have a 2,3-phenanthrene imide, or a 8,9-phenanthrene imide group, or mixtures thereof.

Typically, Q is based on 1,8-naphthalene anhydride, or 1,2-naphthalene anhydride, or mixtures thereof.

Q may be based on a naphthalene anhydride such as 1,8-naphthalic anhydride (when $R_1$=H), 4-nitro-1,8-naphthalic imide or 3-nitro-1,8-naphthalic imide (when one $R_1$=$NO_2$), 4-chloro-1,8-naphthalic imide (when one $R_1$=Cl) group, 4-sulpho-1,8-naphthalic imide or 3-sulpho-1,8-naphthalic imide (when one $R_1$=$SO_3H$), or mixtures thereof.

In one embodiment, when $R_1$ is other than H, the number of non-H groups defined by a may be 1 or 2. When $R_1$ is other than H, the group defined by $R_1$ may be electron-withdrawing (such as $-NO_2$ group, $-SO_3M$ group or a halo group, typically $-Cl$), typically electron-withdrawing. When $R_1$ is electron-withdrawing, the $R_1$ may be either meta-substituted or para-substituted relative to the imide group or mixtures thereof. In one embodiment, the $R_1$ may be meta-substituted relative to the imide group.

In one embodiment, when $R_1$ is other than H, the number of non-H groups defined by a may be 0.

$R_1$ may typically be hydrogen.

R' may be an alkyl or optionally-substituted alkyl having an alkyl group that is linear or branched.

The alkyl groups defined by R' include methyl, ethyl, propyl, butyl, pentyl, hexyl, heptyl, 2-ethylhexyl, nonyl, decyl, undecyl, dodecyl, tridecyl, tetradecyl, pentadecyl, hexadecyl, heptadecyl, octadecyl, nonadecyl, eicosyl, or mixtures thereof. In one embodiment, R' may be derived from an alkanol.

$R_3$ may be H or $C_{1-50}$ (or $C_{1-20}$)-optionally substituted hydrocarbyl group that bonds to a terminal oxygen atom of the polymer chain forming a terminal ether or terminal ester group and may or may not contain a group capable of polymerization such as a vinyl group, or $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof.

$R_3$ may be derived from an alcohol, a thiol, an amine, a carboxylic acid or acid derivative such as an acid halide or an isocyanate or mixtures thereof.

As used herein the term "alk(en)ylene" is intended to include alkylene and alkenylene groups.

The alcohol may be a $C_{1-20}$ alk(en)ylene alcohol, the alk(en)ylene group may be linear or branched. Specific examples of alcohols include methanol, ethanol, n-propanol, isopropanol, n-butanol, 1-methyl-propanol, 2-methylpropanol, tert-butanol, n-pentanol, 1-methylbutanol, 2-methylbutanol, 3-methylbutanol, 2,2-dimethylpropanol, n-hexanol, 1-methylpentanol, 2-methylpentanol, 3-methylpentanol, 4-methylpentanol, 1,1-dimethylbutanol, 2,2-dimethylbutanol, 3,3-dimethyl-butanol, 1,2-dimethylbutanol, n-heptanol, 1-methyl-hexanol, 2-methylhexanol, 3-methylhexanol, 4-methyl-hexanol, 1,2-dimethylpentanol, 1,3-dimethylpentanol, 1,1-dimethylpentanol, 1,1,2,2-tetramethylpropanol, benzyl alcohol, n-octanol, 2-ethylhexanol, n-nonanol, 1-methyloctanol, 2-methyloctanol, n-decanol, n-undecanol, 1-methyldecanol, 2-methyldecanol, n-dodecanol, 2,4-diethyloctanol and the so-called Guerbet alcohols such as those which are commercially available under the trade name Isofol® (ex Sasol) alcohol, or mixtures thereof. Specific examples of Guerbet alcohols include Isofol® 12, 14T, 16, 18T, 18E, 20, 24, 28, 32, 32T and 36.

The amine may be a $C_{1-20}$ alk(en)ylene amine, the alk(en)ylene group may be linear or branched. Specific examples of amines include methylamine, ethylamine, propylamine, butylamine, penylamine, hexylamine, heptylamine, octylamine, nonylamine, decylamine, dodecylamine, tetradecylamine, pentadecylamine, hexadecylamine, octadecylamine, eicosylamine, dimethylamine, diethylamine, propylamine, dibutylamine, dipenylamine, dihexylamine, diheptylamine, dioctylamine, dinonylamine, didecylamine, didodecylamine, ditetradecylamine, dipentadecylamine, dihexadecylamine, dioctadecylamine, dieicosylamine, or mixtures thereof.

The thiol may be a $C_{1-20}$ alk(en)ylene thiol, the alk(en)ylene group may be linear or branched. Specific examples of thiols include Ethanethiol, 1-propanethiol, 2-propanethiol, 1-butanethiol, 2-methyl-1-propanethiol, 1-methyl-1-propanethiol, 1-hexanethiol, 1-octanethiol, 1-dodecanethiol, hexadecylmercaptan, octadecylmercaptan, cyclohexylmercaptan, or mixtures thereof.

The carboxylic acid may be a $C_{1-20}$ alk(en)ylene carboxylic acid, the alk(en)ylene group may be linear or branched. Specific examples of carboxylic acids include acetic acid, methoxyacetic acid, propionic acid, isobutyric acid, 2-methyl butyric acid, isovaleric acid, valeric acid isocaproic acid, caproic acid, heptanoic acid, octanoic acid, 2-ethylhexanoic acid, decanoic acid, dodecanoic acid, tetradecanoic acid, hexadecanoic acid, octadecanoic acid, eicosanoic acid or mixtures thereof.

The isocyanate may be an aromatic or $C_{2-20}$ alk(en)ylene isocyanate, the alk(en)ylene group may be linear or branched. Specific examples include 1-isocyanatorethane, 1-isocyanatopropane, 1-isocyanatobutane, 2-isocyanatobutane, 1-isocyanatopentane 1-isocyanatohexane, 1-isocyanatoheptane, 3-(isocyanatomethyl)heptane, 2-isocyanatoheptane 2-isocyanato-2,4,4-trimethylpentane 1-isocyanatooctane, 2-isocyanatooctane, 1-isocyanatononane, 2-isocyanatononane 1-isocyanatododecane, 1-isocyanatotetradecane, 1-isocyanatoundecane, 1-isocyanatooctadecane, 1-isocyanatopentadecane, 1-isocyanatohexadecane, isocyanatocycloheptane, isocyanatocyclooctane, (isocyanatomethyl)cyclohexane, isocyanatocyclododecane, isocyanatocyclopentane, isocyanatocyclohexane, 1-ethyl-4-(2-isocyanatoethyl)benzene, 1-isocyanato-4-methylbenzene, 1-tert-butyl-4-isocyanatobenzene, 4-isocyanato-1,2-dimethylbenzene, 1-isocyanato-2,4-dimethylbenzene, 2-isocyanato-1,3,5-trimethylbenzene, 1-ethyl-4-isocyanatobenzene, 1-isocyanato-4-isopropylbenzene or mixtures thereof.

The isocyanate may be polymeric, e.g., an alkoxy polyalkylene glycol that is reacted with a diisocyanate. The diisocyanate may include toluene-2,4-diisocyanate, toluene-2,6-diisocyanate, hexamethylene diisocyanate, methylene diphenyl diisocyanate, isophorone diisocyanate, or mixtures thereof.

The acid halide may be a $C_{1-20}$ alk(en)ylene acid chloride, the alk(en)ylene group may be linear or branched. Specific examples of acid chlorides include methanoyl chloride, butanoyl chloride 3,3-dimethylbutanoyl chloride, 3-methylbutanoyl chloride, 2-methylbutanoyl chloride, pentanoyl chloride, heptanoyl chloride, hexanoyl chloride, 2-ethylbutanoyl chloride, decanoyl chloride, 2-ethylhexanoyl chloride, octanoyl chloride, 2-methylpentanoyl chloride, 3,5,5-trimethylhexanoyl chloride, nonanoyl chloride or mixtures thereof.

In one embodiment, $R_3$ may comprise a group capable of polymerization such as a vinyl group. $R_3$ may comprise groups such as (meth)acrylate, styryl, vinyl ether or allyl ether and mixtures thereof. Examples of $R_3$ may be derived from (meth)acrylic acid and their esters, hydroxyl alkyl (meth)acrylates and their polyether derivatives such as hydroxyethyl acrylate or polyethyleneglycol monoacrylate, isocyanatomethyl (meth)acrylates for example isocyanatoethyl methacrylate or isocyanatostyryl derivatives such as 4-isopropenyl-alpha,alpha-dimethylbenzyl isocyanate or mixtures thereof.

W may be oxygen, sulphur, nitrogen, >NH, or >NG, wherein G represents a hydrogen or a hydrocarbyl group containing 1 to 200, or 1 to 100, or 1 to 30 carbon atoms. Typically, W may be oxygen, sulphur or nitrogen. When W is sulphur, the structural group represented by the aromatic ring-$R_2$—W may be formed by reacting an anhydride of the fused aromatic ring with an aminothiol. When W is oxygen, the structural group represented by the aromatic ring-$R_2$—W may be formed by reacting an anhydride of the fused aromatic ring with either an aminoalcohol, or an aminocarboxylic acid. When W is nitrogen (or >NG), the structural group represented by the aromatic ring-$R_2$—W may be formed by reacting an anhydride of the fused aromatic ring with either a diamine, or a polyamine.

Mixtures of all of these can be used i.e., the structural group represented by the aromatic ring-$R_2$—W may be formed by reacting an anhydride of the aromatic ring with a mixture of two, or three, or four, or all five of an aminoalcohol, or an aminocarboxylic acid, an aminothiol, a diamine, or a polyamine. The aromatic ring-$R_2$—W may be formed in a one-pot reaction in the presence of all reactants. Alternatively, a blend of the aromatic ring-$R_2$—W group may be formed by mixing the individual pre-prepared imides.

The cation M, may be a mono- or di-, or tri-valent metal. The metal may for instance be an alkali metal, or alkaline earth metal, or a transition metal. The metal may include lithium, sodium, potassium, calcium, magnesium, barium, zinc, or mixtures thereof.

The polymer chain Pol may be a homopolymer. The polymer chain Pol may be a copolymer. When Pol is a copolymer, the polymer chain may have random or block architecture. Pol may be a homopolymer chain or a copolymer chain, wherein the polymer chain may be selected from the group consisting essentially of a Poly(ether), Poly(ester), Poly(ester amide), Poly(amide), Poly(olefin), and mixtures thereof.

In one embodiment, the polymer chain (Pol) is based on a poly(ether). The poly(ether) may be based on a polyalkylene glycol (typically a poly($C_2$-$C_4$-alkylene glycol or a polyalkarylene glycol (typically a poly $C_8$-glycol)). The polyether may be based on polyalkylene oxides such as ethylene oxide, propylene oxide, butylene oxide and styrene oxide or mixtures thereof. When the polymer chain is a polyether homopolymer, the polyether is not based on ethylene oxide.

In one embodiment, the polymer chain (Pol) is based on a poly(ester). The poly(ester) may be based on a hydroxy-$C_{2\text{-}20}$-alk(en)ylene carboxylic acid monomer or lactone monomer.

Examples of a hydroxy-$C_{2\text{-}20}$-alk(en)ylene carboxylic acid thereof include ricinoleic acid, 12-hydroxy stearic acid, 6-hydroxy caproic acid, 5-hydroxy valeric acid, 12-hydroxy dodecanoic acid, 5-hydroxy dodecanoic acid, 5-hydroxy decanoic acid, 4-hydroxy decanoic acid, 10-hydroxy undecanoic acid, lactic acid glycolic acid, or mixtures thereof.

Examples of a lactone include β-propiolactone, γ-butyrolactone, optional alkyl substituted ε-caprolactone and optionally alkyl substituted δ-valerolactone. The alkyl substituent in ε-caprolactone and δ-valerolactone may be C1-6-alkyl, or C1-4-alkyl, and may be linear or branched. Examples of suitable lactones include ε-caprolactone and the 7-methyl-, 2-methyl-, 3-methyl-, 5-methyl-, 6-methyl-, 4-methyl-, 5-tertbutyl-, 4,4,6-trimethyl- and 4,6,6-trimethyl-analogues, or mixtures thereof.

In one embodiment, the polymer chain (Pol) is based on a poly(ester). The poly(ester) may be based on the reaction of a diol represented by the Formula (i) with a dibasic acid represented by the Formula (ii)

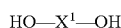  Formula (i)

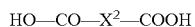  Formula (ii)

wherein
$X^1$ is a linear or branched alkylene group containing from 2 to 20 carbon atoms or a polyalkylene glycol residue with the two hydroxyl groups removed; and
$X^2$ is a linear or branched alk(en)ylene group having 2 to 20 carbon atoms or Ph.

Specific examples of suitable diols include alkylene glycols such as ethylene glycol, propylene glycol, neopentyl glycol, 1,4-butanediol, 1,6-hexanediol, diols with ether linkages such as diethylene glycol, dipropylene glycol, tripropylene glycol and triethylene glycol. Examples of suitable polyalkylene glycols include polyethylene glycols, polypropylene glycols, polybutylene glycols, mixed block and random copolymers of polyethylene glycol and polypropylene glycol (Pluronic™ and reverse Pluronic™ ex BASF) with MW less than 1000. Specific examples of the dibasic acids and anhydrides include maleic anhydride, succinic anhydride, fumaric acid, malonic acid, adipic acid, sebacic acid, phthalic anhydride, oxalic acid, and cyclohexane dicarboxylic anhydride.

In one embodiment, the polymer chain (Pol) is based on a poly(amide). The poly(amide) may be based on the reaction of a diamine represented by the Formula (iii) with a dibasic acid represented by the Formula (iii)

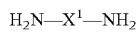  Formula (iii)

wherein
$X^1$ is a linear or branched alkylene group containing from 2 to 20 carbon atoms or a polyalkylene glycol residue with the two amino groups removed;
or the polyamide is obtained/obtainable from the reaction of a lactam, an aminocarboxylic acid or a mixture thereof.

Specific examples of diamines include alkylene diamines such as ethylenediamine, 1,2-propylenediamine, 1,3-propylene diamine, the isomeric butylenediamines, pentanediamines, hexanediamines, heptanediamines, 1,12-diaminododecane and diaminocyclohexanes, and diamines with ether linkages such as 1,2-bis(2-aminoethoxy)ethane. Examples of suitable polyetherdiamines include Jeffamine™ diamines commercially available from Huntsman such as D230, D400, ED600. Specific examples of lactams include laurolactam and caprolactam and the aminocarboxylic acid may be glycine, sarcosine, beta-alanine, 4-aminobutyric acid, 6-aminocaproic acid, 11-aminoundecanoic acid or 12-aminododecanoic acid.

In one embodiment, the polymer chain (Pol) is based on a poly(esteramide). The poly(esteramide) may be based on the reaction of one or more compounds selected from the group of diols (Formula (i)), dibasic acids/anhydrides (Formula (ii)), lactones and hydroxy-$C_{2\text{-}20}$-alk(en)ylene carboxylic acid to prepare the polyester portion and one or more compounds selected from the group of diamines (Formula (iii)), aminocarboxylic acids, lactams and dibasic acids/anhydrides (Formula (ii)) to prepare the polyamide portion. Reaction conditions and process steps for the formation of polyesters using diols, polyesteramides and polyamides are disclosed in U.S. Pat. No. 5,760,257 under Column 5-7.

In one embodiment, the polymer chain (Pol) is based on a Poly(alkylene). The imide of Formula (1) in which the polymer chain (Pol) is represented by a Poly(alkylene) may be obtained/obtainable by a process comprising reacting a polyalkene-substituted amine with a fused aromatic di-acid or anhydride. The polyalkene-substituted amine may be obtained/obtainable from an olefin polymer and an amine, such as, ammonia, diamines, polyamines or mixtures thereof. They may be prepared by a variety of methods such as those described hereinafter.

In one embodiment, the polymer chain (Pol) is based on a poly(ether). In one embodiment, the poly(ether) polymer chain may be incorporated into an imide structure represented by Formula (2):

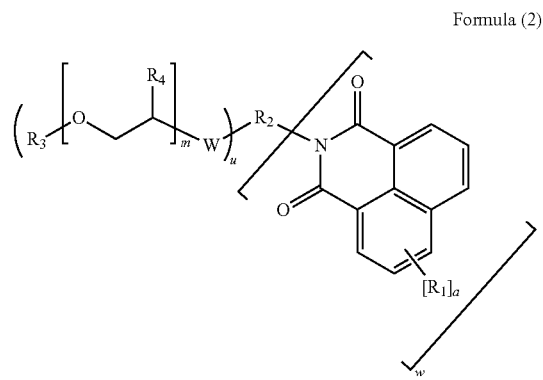

Formula (2)

wherein each variable may independently be
$R_1$ may be a substituent on Q ring in any position available for bonding to a substituent group and $R_1$ is independently represented by one or more of —H, or an electron withdrawing group (such as —CN, —NO$_2$, —SO$_2$NR'$_2$, —C(O)R', —SO$_3$M, —C(O)OM, halo e.g., —Cl or —Br, —NH$_2$, or —OR'), or an electron releasing group (such as —CH$_3$), (typically when R$_1$ is other than —H, the number of non-H groups defined by a may be 0 to 2, 0 to 1, 0, or 1);

W may be oxygen;

M may be H, a metal cation, —NR'$_4{}^+$;

R' may be —H, an optionally-substituted alkyl typically containing 1 to 20, or 1 to 10 carbon atoms, and the substituents may be hydroxyl or halo (typically Cl), or mixtures thereof;

R$_2$ may be a C$_1$ to C$_{20}$, or C$_1$ to C$_{12}$, or C$_1$ to C$_6$ hydrocarbylene group or a C$_1$ to C$_{20}$, or C$_1$ to C$_{12}$, or C$_1$ to C$_6$ hydrocarbonylene group (when R$_2$ contains more than 2 carbon atoms, the hydrocarbylene group or hydrocarbonylene group may be linear or branched) or mixtures thereof;

R$_3$ may be H or C$_{1-50}$ (or C$_{1-20}$)-optionally substituted hydrocarbyl group that bonds to a terminal oxygen atom of the polymer chain forming a terminal ether or terminal ester group and may or may not contain a group capable of polymerization such as a vinyl group, or C$_{1-50}$ (or C$_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof;

R$_4$ may be methyl, ethyl or phenyl when Pol is a homopolymer, and R$_4$ is a mixture of H, methyl, ethyl or phenyl when Pol is a copolymer, providing when R$_4$ is H, it is present in the copolymer chain in an amount sufficient to provide ethylene oxide groups at not more than 60 wt %;

u may be 1 to 3, or 1 to 2, or 1;

w may be 1 to 3, or 1 to 2, or 1;

with the proviso that when R$_2$ is a hydrocarbylene group, u is 1 and w is 1; and m may be 1 to 110, or 1 to 90 or 2 to 90.

In Formula (2), the integer m is such that the polymer chain may have number average molecular weight of 100 to 10,000, 100 to 5000, or 300 to 3000, or 400 to 2500.

An imide of Formula (2) may be prepared by two different processes. The polymer chain of Formula (2) may be referred to as a polyether and the polymer chain may have random or block architecture.

The polyether may contain 0 to 60 wt %, 0 to 50 wt %, 0 to 30 wt %, or 0 to 20 wt %, or 0 to 15 wt % ethylene oxide. The polyether may contain 40 to 100 wt %, 50 to 100 wt %, 70 to 100 wt %, or 80 to 100 wt %, or 85 to 100 wt % of an alkylene oxide having 3 or more carbon atoms (typically 3 or 4, or 3 carbon atoms), an alkarylene oxide having 8 or more carbon atoms (typically 8 carbon atoms) or mixtures thereof.

The polyether may for example be a homopolymer containing propylene glycol or butylene glycol or ethyl benzene glycol or be a random or block copolymer, typically containing at least one of ethylene glycol, butylene glycol, and ethyl benzene glycol copolymerized with propylene glycol.

The polyether may for example be a copolymer of ethylene oxide and propylene oxide. The polyether may be derived from:

0 to 60 wt % ethylene oxide, and 40 to 100 wt % propylene oxide, or 0 to 50 wt % ethylene oxide, and 50 to 100 wt % propylene oxide, or 0 to 30 wt % ethylene oxide, and 70 to 100 wt % propylene oxide, or 0 to 20 wt % ethylene oxide, and 80 to 100 wt % propylene oxide, or 0 to 15 wt % ethylene oxide, and 85 to 100 wt % propylene oxide.

For example the polyether may contain 8 wt % ethylene oxide, and 92 wt % propylene oxide, or 14 wt % ethylene oxide, and 86 wt % propylene oxide.

In one embodiment, the polymer chain may be a poly (ether) of either (i) a polypropylene oxide homopolymer, or (ii) a copolymer of ethylene oxide and propylene oxide.

The first process comprises reacting a polyether amine (typically a polyalkyleneoxide monoalkyl ether monoamine) with a fused aromatic di-acid or anhydride to form the product of formula (2). The reaction to form the imide product of formula (2) may be carried out at a sufficiently high temperature known to the skilled person to favour imide formation e.g., at least 100° C., or 150° C. to 200° C.

The polyetheramine may be prepared by reacting a mono-alcohol initiator with propylene oxide only or with a mixture of propylene oxide and ethylene oxide to form an alcohol-ended polymer chain, followed by conversion of the alcohol-ended polymer chain to an amine. The polyether amine may be commercially available as the Surfonamine® amines from Huntsman Corporation. Specific examples of Surfonamine® amines are B60 (ethylene oxide to propylene oxide ratio of 1 to 9), B100 (propylene oxide), B200 (ethylene oxide to propylene oxide ratio of 6 to 29). The figures in parentheses are approximate repeat units of propylene oxide, and ethylene oxide respectively. The polyetheramine may be obtained by alkoxylation of aminoalcohols as is described in U.S. Pat. No. 5,879,445 (in particular the disclosure in column 2, line 50 to column 7, line 50).

The second process comprises reacting an amino-acid with a fused aromatic di-acid or anhydride to form an acid-functionalised imide and may be carried out at a sufficiently high temperature known to the skilled person to favour imide formation e.g., at least 100° C., or 150° C. to 200° C.; and esterifying the acid-functionalised imide with a polyalkylene glycol mono-substituted C$_{1-20}$ alk(en)ylene ether, the reaction temperature may be 50° C. to 250° C. or 150° C. to 200° C., optionally in the presence of an esterification catalyst.

The polyalkylene glycol mono-substituted C$_{1-20}$ alk(en)ylene ether may be a homopolymer containing propylene glycol or butylene glycol or phenylene glycol or be a random or block copolymer, typically containing at least one of ethylene glycol, butylene glycol, and phenylene glycol copolymerized with propylene glycol.

The polyalkylene glycol mono-substituted C$_{1-20}$ alk(en)ylene ether may be methoxy polypropylene glycol, ethoxy polypropylene glycol, propoxy polypropylene glycol, butoxy polypropylene glycol, alkoxy(polyethyleneglycol co-polypropyleneglycol), polypropyleneglycol mono(meth) acrylate or mixtures thereof.

In one embodiment, the polymer chain (Pol) is based on a poly(ether). The poly(ether) may be based on a polyalkylene glycol (typically a poly(C$_2$-C$_4$-alkylene glycol). In one embodiment, the poly(ether) polymer chain may be incorporated into an imide structure represented by Formula (3a):

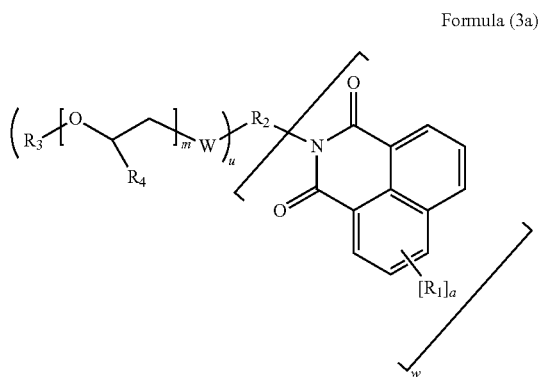

Formula (3a)

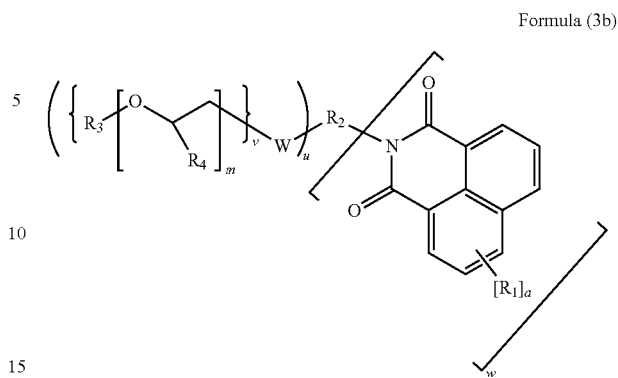

Formula (3b)

wherein each variable may independently be $R_1$ may be a substituent on Q ring in any position available for bonding to a substituent group and $R_1$ is independently represented by one or more of —H, or an electron withdrawing group (such as —CN, —$NO_2$, —$SO_2NR'_2$, —C(O)R', —$SO_3M$, —C(O)OM, halo e.g., —Cl or —Br, —$NH_2$, or —OR'), or an electron releasing group (such as —$CH_3$), (typically when $R_1$ is other than —H, the number of non-H groups defined by a may be 0 to 2, 0 to 1, 0, or 1). For example $R_1$ may be —H, —$CH_3$, —Cl, —$NO_2$, —$SO_3M$, or —C(O)OM (typically when a is non-zero $R_1$ may be —Cl, —$SO_3M$ or —$NO_2$);

W may be sulphur, >NG, or oxygen or mixtures thereof (typically oxygen);

G may be a hydrocarbyl group containing 1 to 200, or 1 to 100, or 1 to 30 carbon atoms;

M may be H, a metal cation, —$NR'_4^+$;

R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbylene group or a $C_1$ to $C_{20}$, or $C_1$ to $C_{12}$, or $C_1$ to $C_6$ hydrocarbonylene group or mixtures thereof;

$R_3$ may be H or $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof;

$R_4$ may be methyl, ethyl or phenyl when Pol is a homopolymer, and $R_4$ is a mixture of H, methyl, ethyl or phenyl when Pol is a copolymer, providing when $R_4$ is H, it is present in the copolymer chain in an amount sufficient to provide ethylene oxide groups at not more than 60 wt %;

u may be 1 to 3, or 1 to 2, or 1;

w may be 1 to 3, or 1 to 2, or 1; and m may be 1 to 110, or 1 to 90.

The polymer of the invention may have multiple polymer chain types attached to the group W. In one embodiment, the polymer chain (Pol) is based on a poly(ether). The poly(ether) may be based on a polyalkylene glycol (typically a poly($C_2$-$C_4$-alkylene glycol). In one embodiment, the poly(ether) polymer chain may be incorporated into an imide structure represented by Formula (3b):

wherein

W is N (formed when $R^2$ of formula (1) is derived from a diamine or a polyamine);

$R_2$ is a $C_1$ to $C_{20}$, or $C_1$ to $C_{12}$, or $C_1$ to $C_6$ hydrocarbylene group;

v is 2;

and wherein all other variables are defined above.

In Formula (3a) and (3b), the integer m is such that the polymer chain may have number average molecular weight of 100 to 10,000, or 100 to 5000, or 300 to 3000, or 400 to 2500.

An imide of Formula (3a) and (3b) may be prepared by different processes. The polymer chain of Formula (3a) and (3b) may be referred to as a poly(ether).

Formula (3a) may be prepared by a process that comprises reacting an aminoalcohol with a fused aromatic di-acid or anhydride to form a hydroxyl-functionalised fused aromatic imide, and then reacting the hydroxyl-functionalised fused aromatic imide with an oxirane (such as propylene oxide, butylene oxide, or styrene oxide or a mixture of propylene oxide with ethylene oxide, butylene oxide, styrene oxide or mixtures thereof), or a carbonate (such as ethylene carbonate, or propylene carbonate) to form the polymer of the invention of Formula (3a) where $R_3$ is —H. The first step of the reaction (to form the imide) may be carried out at a sufficiently high temperature known to the skilled person to favour imide formation e.g., at least 100° C., or 150° C. to 200° C., or at least 100° C., or 150° C. to 250° C. The second step of the reaction to react the imide with an oxirane is carried out at a sufficiently high temperature known to the skilled person, e.g., at least 100° C., or 150° C. to 200° C. in the presence of a base catalyst. Typically, a temperature in the range of 150° C. to 250° C. may be employed when a carbonate is used.

Formula (3a) may also be prepared by a process that comprises reacting an amino acid with a fused aromatic di-acid or anhydride to form an acid-functionalised fused aromatic imide, and then reacting the acid-functionalised fused aromatic imide with an oxirane (such as ethylene oxide, propylene oxide, butylene oxide, or styrene oxide or mixtures thereof) to form the polymer of the invention of Formula (3a) where $R_3$ is —H, using the process conditions stated above.

Formula (3a) may also be prepared by a process that comprises reacting an amino-thiol, to form an thiol-functionalised fused aromatic imide, and then reacting the thiol-functionalised fused aromatic imide with an oxirane (such as ethylene oxide, propylene oxide, butylene oxide, or styrene oxide or mixtures thereof) or a carbonate (such as ethylene carbonate, or propylene carbonate) to form the polymer of the invention of Formula (3a) where $R_3$ is —H, using the process conditions stated above.

Formulae (3a) and (3b) may be prepared by a process that comprises reacting a diamine with a fused aromatic di-acid or anhydride to form an amino-functionalised fused aromatic imide and then reacting the amino-functionalised fused aromatic imide with an oxirane (such as ethylene oxide, propylene oxide, butylene oxide, or styrene oxide or mixtures thereof) or a carbonate (such as ethylene carbonate, or propylene carbonate) to form the polymer of the invention of Formula (3a) and (3b) where $R_3$ is —H, using the process conditions stated above.

The reaction of either the hydroxyl-functionalised fused aromatic imide or thiol-functionalised fused aromatic imide or acid-functionalised fused aromatic imide or amine-functionalised fused aromatic imide, with the oxirane in the processes described above may be carried out at a temperature of 100° C. to 200° C. in the presence of a base such as potassium hydroxide or sodium hydroxide.

In one embodiment, the poly(ether) polymer chain of the imide structure represented by Formula (3a) and (3b) where $R_3$ is a —H, may be capped by a $C_{1-50}$ (or $C_{1-20}$)-hydrocarbonyl group (i.e., a hydrocarbyl group containing a carbonyl group). $R_3$ may be obtained/obtainable from a carboxylic acid, an acid derivative such as an acid halide, an isocyanate or mixtures thereof. The reaction conditions for capping the polymer chain to form the polymer of Formula (3a) and (3b) where $R_3$ may be a $C_{1-50}$ (or $C_{1-20}$)-hydrocarbonyl group (i.e., a hydrocarbyl group containing a carbonyl group), are reactions known in the art.

In Formulae (2) and (3), a polar organic medium dispersant may be formed when the polyether contains at least 50 wt % to 100 wt % propylene oxide.

In Formulae (2) and (3), a polar organic medium dispersant may be formed when the polyether contains at least 0 wt % to 40 wt % ethylene oxide. However, the amount of ethylene oxide may also be modified by those skilled in the art of preparing a non-polar organic medium or a polar organic medium dispersant to produce a dispersant with up to 49.99 wt % ethylene oxide.

Typically, the polymer chain (Pol) of Formulae (2) and (3) contains 60 wt % to 100 wt % propylene oxide, or 80 wt % to 100 wt %, or 100 wt % propylene oxide; and 0 wt % to 40 wt %, or 0 wt % to 20 wt %, or 0 wt % ethylene oxide.

In one embodiment, the polymer of the invention may be represented by Formula (4a), i.e., the polymer may be a poly(ester), a poly(esteramide), or a poly(amide):

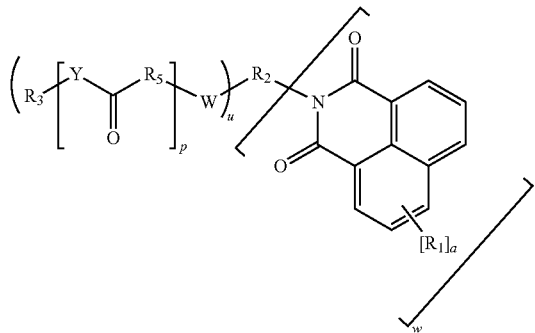

Formula (4a)

wherein each variable may independently be $R_1$ may be a substituent on Q ring in any position available for bonding to a substituent group and $R_1$ is independently represented by one or more of —H, or an electron withdrawing group (such as —CN, —NO$_2$, —SO$_2$NR'$_2$, —C(O)R', —SO$_3$M, —C(O)OM, halo e.g., —Cl or —Br, —NH$_2$, or —OR'), or an electron releasing group (such as —CH$_3$), (typically when $R_1$ is other than —H, the number of non-H groups defined by a may be 0 to 2, 0 to 1, 0, or 1);

W is oxygen or >NG;

G may be hydrogen or a hydrocarbyl group containing 1 to 200, or 1 to 100, or 1 to 30 carbon atoms;

M may be H, a metal cation, NR'$_4^+$;

R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbonylene group;

$R_3$ may be H or $C_{1-50}$ (or $C_{1-20}$)-optionally substituted hydrocarbyl group that bonds to a terminal oxygen atom of the polymer chain forming a terminal ester group and may or may not contain a group capable of polymerization such as a vinyl group, and the substituent may be halo, ether, ester, or mixtures thereof;

$R_5$ may be a $C_{1-19}$-hydrocarbylene group;

Y may be oxygen or >NG;

p may be 2-120;

u may be 1 to 3, or 1 to 2, or 1; and w may be 1 to 3, or 1 to 2, or 1.

In one embodiment, the polymer of the invention may be represented by Formula (4b), i.e., the polymer may be a poly(ester), a poly(esteramide), or a poly(amide):

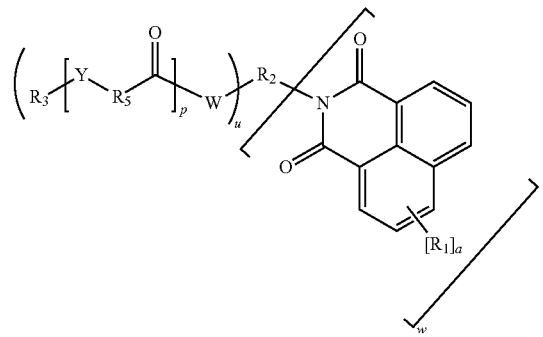

Formula (4b)

wherein each variable may independently be $R_1$ may be a substituent on Q ring in any position available for bonding to a substituent group and $R_1$ is independently represented by one or more of —H, or an electron withdrawing group (such as —NO$_2$, —SO$_2$NR'$_2$, —C(O)R', —SO$_3$M, —C(O)OM, halo e.g., —Cl or —Br, —NH$_2$, or —OR'), or an electron releasing group (such as —CH$_3$), (typically when $R_1$ is other than —H, the number of non-H groups defined by a may be 0 to 2, 0 to 1, 0, or 1);

W may be sulphur, >NG, or oxygen (typically oxygen);

G may be hydrogen or a hydrocarbyl group containing 1 to 200, or 1 to 100, or 1 to 30 carbon atoms;

M may be H, a metal cation, —NR'$_4^+$, or mixtures thereof

R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbylene group, $R_3$ may be H or $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof.

$R_5$ may be a $C_{1-19}$-hydrocarbylene group;

Y may be oxygen or >NG;

p may be 2-120;

u may be 1 to 3, or 1 to 2, or 1; and w may be 1 to 3, or 1 to 2, or 1.

The polymer chain of Formulae (4a) or (4b) may have a number average molecular weight of 200 to 10,000, or 300 to 5000, or 500 to 3000, or 600 to 2500. Typically, the polymer chain of Formulae (4a) or (4b) may have number average molecular weight of 600 to 2500.

An imide of Formula (4a) where $R_3$ is —H, may be prepared by a process comprising reacting an amino acid with a fused aromatic di-acid or anhydride to form an acid-functionalised fused aromatic imide, and then reacting acid-functionalised fused aromatic imide with one or more of a hydroxy-$C_{2-20}$-alk(en)ylene carboxylic acid, a lactone, an aminocarboxylic acid or mixtures thereof. The reaction of the acid-functionalised fused aromatic imide, with the hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

In one embodiment, an imide represented by Formula (4a) where $R_3$ is a $C_{1-50}$ (or $C_{1-20}$)-hydrocarbyl group, may be prepared by reacting an imide of Formula (4a) where $R_3$ is —H with an alcohol, an amine, a thiol or mixtures thereof. The reaction conditions for capping the polymer chain to result in the polymer of the present invention with an alcohol, an amine, or a thiol are known in the art.

Alternatively, the imide of Formula (4a) where $R_3$ may be a $C_{1-50}$ (or $C_{1-20}$)-hydrocarbyl group, may be prepared by a process comprising reacting an amino acid with a fused aromatic di-acid or anhydride to form an acid-functionalised fused aromatic imide, and then reacting acid-functionalised fused aromatic imide with one or more of a hydroxyl-functionalised polyester, a hydroxyl-functionalised polyesteramide, an amino-functionalised polyesteramide or an amino-functionalized polyamide, the reaction may be carried out at a temperature of 50° C. to 250° C. or 150° C. to 200° C., optionally in the presence of a catalyst. The hydroxyl-functionalised polyester is obtained/obtainable from the polymerisation of one or more of a hydroxy-$C_{2-20}$-alkylene carboxylic acid, a lactone or mixtures thereof, with a $C_{1-50}$ (or $C_{1-20}$)-optionally substituted hydrocarbyl group and is conveniently performed at a temperature of 50° C. to 250° C. or 150° C. to 200° C., optionally in the presence of an esterification catalyst as disclosed in U.S. Pat. No. 4,861,380.

The amino- or hydroxyl-functionalised polyesteramide is obtained/obtainable from the polymerisation of one or more of a hydroxy-$C_{2-20}$-alkylene carboxylic acid, a lactone or mixtures thereof, with one or more of an aminocarboxylic acid and a $C_{1-50}$ (or $C_{1-20}$)-optionally substituted hydrocarbyl group and is conveniently performed at a temperature of 50° C. to 250° C. or 150° C. to 200° C., optionally in the presence of an esterification catalyst as disclosed in U.S. Pat. No. 5,760,257.

The amino-functionalised poly(amide) is obtained/obtainable from the polymerisation of one or more of an aminocarboxylic acid with a $C_{1-50}$ (or $C_{1-20}$)-optionally substituted hydrocarbyl group and is conveniently performed at a temperature of 50° C. to 250° C. or 150° C. to 200° C., optionally in the presence of a catalyst, as disclosed in U.S. Pat. No. 5,760,257.

An imide of Formula (4b) where $R_3$ is —H, may be prepared by a process comprising reacting an amino alcohol with a fused aromatic di-acid or anhydride to form an hydroxyl-functionalised fused aromatic imide, and then reacting hydroxyl-functionalised fused aromatic imide with one or more of a hydroxy-$C_{2-20}$-alk(en)ylene carboxylic acid, a lactone, an aminocarboxylic acid or mixtures thereof. The reaction of the hydroxyl-functionalised fused aromatic imide, with the hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

An imide of Formula (4b) where $R_3$ is —H, may be prepared by a process comprising reacting an amino thiol with a fused aromatic di-acid or anhydride to form a thiol-functionalised fused aromatic imide, and then reacting thiol-functionalised fused aromatic imide with one or more of a hydroxy-$C_{2-20}$-alk(en)ylene carboxylic acid, a lactone, an aminocarboxylic acid or mixtures thereof. The reaction of the thiol-functionalised fused aromatic imide, with the hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

An imide of Formula (4b) where $R_3$ is —H, may be prepared by a process comprising reacting a diamine or polyamine with a fused aromatic di-acid or anhydride to form an amino-functionalised fused aromatic imide, and then reacting amino-functionalised fused aromatic imide with one or more of a hydroxy-$C_{2-20}$-alk(en)ylene carboxylic acid, a lactone, an aminocarboxylic acid or mixtures thereof. The reaction of the amino-functionalised fused aromatic imide, with the hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

In one embodiment, an imide represented by Formula (4b) where $R_3$ is a $C_{1-50}$ (or $C_{1-20}$)-hydrocarbonyl group (i.e., a hydrocarbyl group containing a carbonyl group), may be prepared by reacting an imide of Formula (4b) where $R_3$ is —H with a carboxylic acid, an acid derivative such as an acid halide, an isocyanate or mixtures thereof. The reaction conditions for capping the polymer chain to result in the polymer of the present invention with an acid, acid derivative, or an isocyanate are reactions known in the art.

Alternatively, the imide of Formula (4b) where $R_3$ may be a $C_{1-50}$ (or $C_{1-20}$)-hydrocarbonyl group (i.e., a hydrocarbyl group containing a carbonyl group), may be prepared by a process comprising reacting an amino alcohol or an amino thiol or a diamine or a polyamine with a fused aromatic di-acid or anhydride to form a hydroxyl-functionalised fused aromatic imide or a thiol-functionalised fused aromatic imide or an amino-functionalised fused aromatic imide respectively, and then reacting such fused aromatic imides with one or more of an acid-functionalised polyester, acid-functionalised polyesteramide or acid functionalized polyamide or mixtures thereof, the reaction may be carried out at a temperature of 50° C. to 250° C. or 150° C. to 200° C., optionally in the presence of a catalyst. The acid-functionalised polyester, acid-functionalised polyesteramide or acid functionalized polyamide is derivable by the polymerisation of one or more of a hydroxy-$C_{2-20}$-alkylene carboxylic acid, a lactone, an aminocarboxylic acid or mixtures thereof with a $C_{1-50}$ (or $C_{1-20}$)-optionally substituted hydrocarbonyl group and is conveniently performed at a temperature of 50° C. to 250° C. or 150° C. to 200° C., optionally in the presence of a catalyst, as disclosed in U.S. Pat. No. 5,760,270.

Examples of a hydroxy-$C_{2-20}$-alk(en)ylene carboxylic acid thereof include ricinoleic acid, 12-hydroxy stearic acid, 6-hydroxy caproic acid, 5-hydroxy valeric acid, 12-hydroxy dodecanoic acid, 5-hydroxy dodecanoic acid, 5-hydroxy decanoic acid, 4-hydroxy decanoic acid, 10-hydroxy undecanoic acid, lactic acid glycolic acid, or mixtures thereof Examples of a lactone include β-propiolactone, γ-butyrolactone, optional alkyl substituted ε-caprolactone and optionally alkyl substituted δ-valerolactone. The alkyl substituent in ε-caprolactone and δ-valerolactone may be C1-6-alkyl, or C1-4-alkyl, and may be linear or branched. Examples of suitable lactones are ε-caprolactone and the 7-methyl-, 2-methyl-, 3-methyl-, 5-methyl-, 6-methyl-, 4-methyl-, 5-tertbutyl-, 4,4,6-trimethyl- and 4,6,6-trimethyl-analogues or mixtures thereof.

Examples of an aminocarboxylic acid include 11-amino undecanoic acid, 12-amino dodecanoic acid, 6-amino caproic acid, 4-aminobutyric acid, 3-alanine, glycine, and sarcosine or mixtures thereof.

In one embodiment, the polymer of the invention may be represented by Formula (5), (i.e., the polymer may be a poly(ester) co-polyether, a poly(esteramide) co-poly(ether), or a poly(amide) co-poly(ether)):

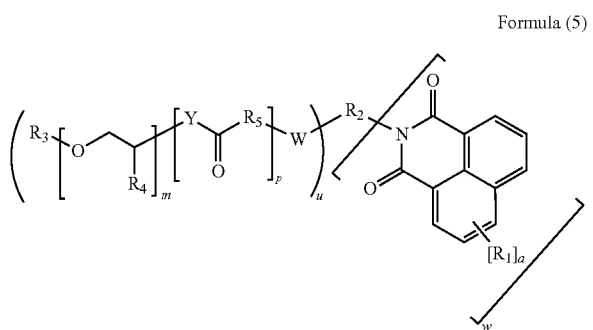

Formula (5)

wherein each variable may independently be $R_1$ may be a substituent on Q ring in any position available for bonding to a substituent group and $R_1$ is independently represented by one or more of —H, or an electron withdrawing group (such as —CN, —$NO_2$, —$SO_2NR'_2$, —C(O)R', —$SO_3M$, —C(O)OM, halo e.g., —Cl or —Br, —$NH_2$, or —OR'), or an electron releasing group (such as —$CH_3$), (typically when $R_1$ is other than —H, the number of non-H groups defined by a may be 0 to 2, 0 to 1, 0, or 1);

W is oxygen or >NG;

G may be hydrogen or a hydrocarbyl group containing 1 to 200, or 1 to 100, or 1 to 30 carbon atoms;

M may be H, a metal cation, $NR'_4{}^+$;

R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbonylene group;

$R_3$ may be a $C_{1-50}$ (or $C_{1-20}$)-optionally substituted hydrocarbyl group that bonds to a terminal oxygen atom of the polymer chain forming a terminal ether group and may or may not contain a group capable of polymerization such as a vinyl group, or a $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof;

$R_4$ may be H, methyl, ethyl or phenyl or mixtures thereof;

$R_5$ may be a $C_{1-19}$-hydrocarbylene group;

Y is oxygen or >NG;

u may be 1 to 3, or 1 to 2, or 1;

w may be 1 to 3, or 1 to 2, or 1;

q may be 1 to 90; and m may be 1 to 90.

The polymer chain of Formula (5) may have a number average molecular weight of 200 to 10,000, or 300 to 5000, or 500 to 3000, or 1000 to 2500. Typically, the polymer chain of Formula (5) may have number average molecular weight of 1000 to 2500.

An imide of Formula (5) may be prepared by a process comprising steps:

(i) reacting an amino acid with a fused aromatic di-acid or anhydride to form an acid-functionalised fused aromatic imide, and then reacting acid-functionalised fused aromatic imide with one or more of a hydroxy-$C_{2-20}$-alk(en)ylene carboxylic acid, a lactone, an aminocarboxylic acid or mixtures thereof. The reaction of the acid-functionalised fused aromatic imide, with the hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst; and (ii) reacting a product of step (i) with a polyalkylene glycol mono-substituted $C_{1-20}$ alk(en)ylene ether, optionally in the presence of an esterification catalyst.

Alternatively, the polymer of Formula (5) may be obtained/obtainable by reacting:

(i) a polyalkylene glycol mono-substituted $C_{1-20}$ alk(en)ylene ether with one or more of a hydroxy-$C_{2-20}$-alk(en)ylene carboxylic acid, a lactone, an aminocarboxylic acid or mixtures thereof, at a temperature of 50° C. to 250° C. or 150° C. to 200° C. to form a hydroxyl- and/or amino-terminated polymer; and (ii) reacting the product of (i) with an acid-functionalised fused aromatic imide at a temperature of 50° C. to 250° C. or 150° C. to 200° C., optionally in the presence of a catalyst.

In one embodiment, the polymer chain (Pol) is based on a poly(ether) co-poly(ester). The poly(ether) co-poly(ester) may be based on a polyalkylene glycol (typically a poly($C_2$-$C_4$-alkylene glycol) and a lactone, or a hydroxy-$C_{2-20}$-alk(en)ylene carboxylic acid or mixtures thereof.

In one embodiment, the polymer of the invention may be represented by Formula (6a), (i.e., the polymer may be a poly(ether) co-poly(ester), a poly(ether) co-poly(esteramide) or a poly(ether) co-poly(amide):

Formula (6a)

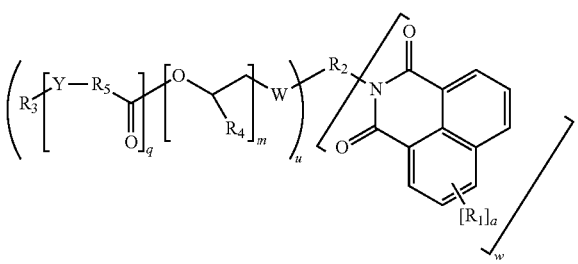

wherein each variable may independently be
$R_1$ may be a substituent on Q ring in any position available for bonding to a substituent group and $R_1$ is independently represented by one or more of —H, or an electron withdrawing group (such as —CN, —NO$_2$, —SO$_2$NR'$_2$, —C(O)R', —SO$_3$M, —C(O)OM, halo e.g., —Cl or —Br, —NH$_2$, or —OR'), or an electron releasing group (such as —CH$_3$), (typically when $R_1$ is other than —H, the number of non-H groups defined by a may be 0 to 2, 0 to 1, 0, or 1); W may be sulphur, >NG, or oxygen (typically oxygen or >NG); M may be H, a metal cation, NR'$_4^+$;
R' may be —H, an optionally-substituted alkyl typically containing 1 to 20, or 1 to 10 carbon atoms, and the substituents may be hydroxyl or halo (typically Cl) or mixtures thereof;
$R_2$ may be a $C_1$ to $C_{20}$, or $C_1$ to $C_{12}$, or $C_1$ to $C_6$ hydrocarbylene group or a $C_1$ to $C_{20}$, or $C_1$ to $C_{12}$, or $C_1$ to $C_6$ hydrocarbonylene group or mixtures thereof;
G may be hydrogen or a hydrocarbyl group containing 1 to 200, or 1 to 100, or 1 to 30 carbon atoms;
$R_3$ may be H or $C_{1-50}$ (or $C_{1-20}$)-hydrocarbonyl group (i.e., a hydrocarbyl group containing a carbonyl group) that bonds to the oxygen atom of the polymer chain forming a terminal ester group or terminal urethane group and may or may not contain a group capable of polymerization such as a vinyl group, and the substituent may be halo, ether, ester, or mixtures thereof;
$R_4$ may be H, methyl, ethyl or phenyl or mixtures thereof;
$R_5$ may be a $C_{1-19}$-hydrocarbylene group;
Y may be oxygen or >NG;
u may be 1 to 3, or 1 to 2, or 1;
w may be 1 to 3, or 1 to 2, or 1;
q may be 1 to 90 and m may be 1 to 90.

In one embodiment, the polymer of the invention may be represented by Formula (6b), (i.e., the polymer may be a poly(ether) co-poly(ester), a poly(ether) co-poly(ester-amide) or a poly(ether) co-poly(amide):

Formula (6b)

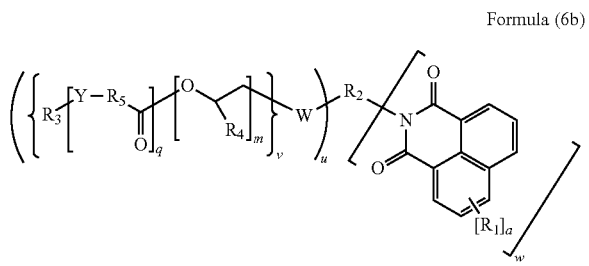

wherein
W is N (formed when $R^2$ of formula (1) is derived from a diamine or a polyamine);

$R_2$ is a $C_1$ to $C_{20}$, or $C_1$ to $C_{12}$, or $C_1$ to $C_6$ hydrocarbylene group;
v is 2; and
wherein all other variables are defined above.

The polymer chain of Formulae (6a) or (6b) may have a number average molecular weight of 200 to 10,000, or 300 to 5000, or 500 to 3000, or 600 to 2500. Typically the polymer chain of Formulae (6a) or (6b) may have number average molecular weight of 1000 to 2500.

Formula (6a) may be prepared by a process that comprises reacting an imide of Formula (3a) where $R_3$ is —H, with one or more of a hydroxy-$C_{2-20}$-alk(en)ylene carboxylic acid, a lactone, an aminocarboxylic acid or mixtures thereof. The reaction of the imide of Formula (3a) where $R_3$ is —H, with a hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

Formula (6b) may be prepared by a process that comprises reacting an imide of Formula (3b) where $R_3$ is —H, with one or more of a hydroxy-$C_{2-20}$-alk(en)ylene carboxylic acid, a lactone, an aminocarboxylic acid or mixtures thereof. The reaction of the imide of Formula (3a) where $R_3$ is —H, with the a hydroxy-$C_{2-20}$-alk(en)ylene carboxylic acid, a lactone, an aminocarboxylic acid or mixture thereof may be carried out at a temperature of 50° C. to 250° C. or 150° C. to 200° C., optionally in the presence of a catalyst.

In one embodiment, an imide represented by Formula (6a) or (6b) where $R_3$ is a $C_{1-50}$ (or $C_{1-20}$)-hydrocarbonyl group (i.e., a hydrocarbyl group containing a carbonyl group), may be prepared by reacting an imide of Formula (6a) or (6b) where $R_3$ is —H respectively, with a carboxylic acid, an acid derivative such as an acid halide, an isocyanate or mixtures thereof. The reaction conditions for capping the polymer chain to result in the polymers of the present invention with an acid, an acid derivative, or an isocyanate are reactions known in the art.

Alternatively, the imide of Formula (6a) or (6b) where $R_3$ may be a $C_{1-50}$ (or $C_{1-20}$)-hydrocarbonyl group (i.e., a hydrocarbyl group containing a carbonyl group), may be prepared by reacting an imide of Formula (3a) or (3b) where $R_3$ is —H respectively, with one or more of an acid-functionalised polyester, acid-functionalised polyesteramide or acid functionalized polyamide or mixtures thereof, the reaction may be carried out at a temperature of 50° C. to 250° C. or 150° C. to 200° C., optionally in the presence of a catalyst. The acid-functionalised polyester, acid-functionalised polyesteramide or acid functionalized polyamide is derivable by the polymerisation of one or more of a hydroxy-$C_{2-20}$-alkylene carboxylic acid, a lactone, an aminocarboxylic acid or mixtures thereof with a $C_{1-50}$ (or $C_{1-20}$)-optionally substituted hydrocarbonyl group and is conveniently performed at a temperature of 50° C. to 250° C. or 150° C. to 200° C., optionally in the presence of a catalyst, as disclosed in U.S. Pat. No. 5,760,270.

In one embodiment, the polymer chain (Pol) is based on a Poly(alkylene). In one embodiment, the Poly(alkylene) polymer chain may be incorporated into an imide structure represented by Formula (7):

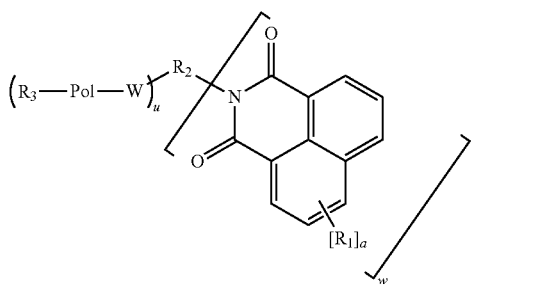

Formula (7)

wherein each variable may independently be $R_1$ may be a substituent on Q ring in any position available for bonding to a substituent group and $R_1$ is independently represented by one or more of —H, or an electron withdrawing group (such as —CN, —$NO_2$, —$SO_2NR'_2$, —C(O)R', —$SO_3M$, —C(O)OM, halo e.g., —Cl or —Br, —$NH_2$, or —OR'), or an electron releasing group (such as —$CH_3$), (typically when $R_1$ is other than —H, the number of non-H groups defined by a may be 0 to 2, 0 to 1, 0, or 1);

W may be sulphur, nitrogen, >NH, or >NG, or oxygen (typically oxygen, nitrogen or >NG);

M may be H, a metal cation, $NR'_4{}^+$, or mixtures thereof;

R' may be —H, an optionally-substituted alkyl typically containing 1 to 20, or 1 to 10 carbon atoms, and the substituents may be hydroxyl or halo (typically Cl) or mixtures thereof;

$R_2$ may be a $C_1$ to $C_{20}$, or $C_1$ to $C_{12}$, or $C_1$ to $C_6$ hydrocarbylene group or a $C_1$ to C20, or $C_1$ to $C_{12}$, or $C_1$ to $C_6$ hydrocarbonylene group or mixtures thereof; G may be hydrogen or a hydrocarbyl group containing 1 to 200, or 1 to 100, or 1 to 30 carbon atoms;

$R_3$ is H;

u is 1;

w is 1 to 3; and

Pol is a polyisobutylene chain when W is >NG, or a polyisobutylene succinic anhydride attached to W to form an imide when W is N, and to form an amide or ester when W is >NG or oxygen respectively.

The polymer chain (Pol) of Formula (7) may have a number average molecular weight of 200 to 10,000, or 300 to 5000, or 500 to 3000, or 600 to 2500. Typically, the polymer chain of Formula (7) may have number average molecular weight of 1000 to 2500.

In one embodiment, an imide represented by Formula (7) may be prepared by a process comprising steps:
(i) reacting an amino acid with a fused aromatic di-acid or anhydride to form an acid-functionalised fused aromatic imide, and
(ii) then reacting acid-functionalised fused aromatic imide with a polyisobutyleneamine (obtained/obtainable from an olefin polymer and an amine) or mixture thereof.

The first step of the reaction (to form the imide) may be carried out at a sufficiently high temperature known to the skilled person to favour imide formation e.g., at least 100° C., or 150° C. to 200° C. The reaction of the acid-functionalised fused aromatic imide, with the polyisobutyleneamine or mixtures thereof may be carried out at a temperature of 50° C. to 250° C. or 150° C. to 200° C., optionally in the presence of a catalyst.

In one embodiment, an imide represented by Formula (7) where W is oxygen, may be prepared by a process that comprises reacting an aminoalcohol with a fused aromatic di-acid or anhydride to form a hydroxyl-functionalised fused aromatic imide, and then reacting the hydroxyl-functionalised fused aromatic imide with a polyisobutylene succinic anhydride (PIBSA). The first step of the reaction (to form the imide) may be carried out at a sufficiently high temperature known to the skilled person to favour imide formation e.g., at least 100° C., or 150° C. to 200° C., or at least 100° C., or 150° C. to 250° C. The second step of the reaction to react the imide with a PIBSA is carried out at a sufficiently high temperature known to the skilled person, e.g., at least 100° C., or 150° C. to 200° C., optionally in the presence of a catalyst.

Formula (7) may also be prepared by a process that comprises reacting an amino-thiol, to form a thiol-functionalised fused aromatic imide, and then reacting the thiol-functionalised fused aromatic imide with a PIBSA, using the process conditions stated above.

Formula (7) may also be prepared by a process that comprises reacting a diamine with a fused aromatic di-acid or anhydride to form an amino-functionalised fused aromatic imide and then reacting the amino-functionalised fused aromatic imide with a PIBSA to form the polymer of the invention of Formula (7) where W is nitrogen, or >NG, using the process conditions stated above.

The invention also provides for a polymer comprising a polymer chain having at least one fused aromatic imide pendant group, wherein the chain may be prepared directly by reacting a fused aromatic di-acid or anhydride with one or more of a polyalkyleneamine (obtained/obtainable from an olefin polymer and an amine). The reaction of the fused aromatic di-acid or anhydride with one or more of a polyalkyleneamine may be carried out at a sufficiently high temperature known to the skilled person to favour imide formation e.g., at least 100° C., or 150° C. to 200° C., or at least 100° C., or 150° C. to 250° C. Examples of polyalkyleneamines include polyisobutyleneamines commercially available as FD-100™ and Kerocom™ Piba03 available from BASF.

One method of preparation of a polyalkene-substituted amine involves reacting a halogenated olefin polymer with an amine, as disclosed in U.S. Pat. Nos. 3,275,554; 3,438,757; 3,454,555; 3,565,804; 3,755,433; and 3,822,289.

Another method of preparation of a polyalkene-substituted amine involves reaction of a hydroformylated olefin with a polyamine and hydrogenating the reaction product, as disclosed in U.S. Pat. Nos. 5,567,845 and 5,496,383.

Another method of preparation of a polyalkene-substituted amine involves converting a polyalkene by means of a conventional epoxidation reagent with or without a catalyst, into the corresponding epoxide and converting the epoxide into the polyalkene substituted amine by reaction with ammonia or an amine under the conditions of reductive amination, as disclosed in U.S. Pat. No. 5,350,429.

Another method for preparing polyalkene-substituted amine involves hydrogenation of a β-aminonitrile, which is made by reacting an amine with a nitrile, as disclosed in U.S. Pat. No. 5,492,641.

Yet another method for preparing polyalkene-substituted amine involves hydroformylating a polybutene or polyisobutylene with a catalyst, such as, rhodium or cobalt, in the presence of CO and $H_2$ at elevated pressures and temperatures, as disclosed in U.S. Pat. No. 4,832,702.

The above methods for the preparation of polyalkene substituted amine are for illustrative purposes only and are not meant to be an exhaustive list. The polyalkene-substituted amines of the present invention are not limited in scope to the methods of their preparation disclosed hereinabove.

In one embodiment, the olefin polymers used to make the polyalkene-substituted amine of the present invention are derived from olefin polymers. The olefin polymers include homopolymers and interpolymers of polymerizable olefin monomers of 2 to 16 carbon atoms, and in one embodiment from 2 to 6 carbon atoms, and in one embodiment from 2 to 4 carbon atoms. The interpolymers are those in which two or more olefin monomers are interpolymerized according to well known conventional procedures to form polyalkenes having units within their structure derived from each of said two or more olefin monomers. Thus "interpolymer(s)" as used herein is inclusive of copolymers, terpolymers, and tetrapolymers. As will be apparent to those of ordinary skill in the art, the polyalkenes from which the polyalkene-substituted amines (a) are derived, are often conventionally referred to as "polyolefin(s)".

The olefin monomers from which the olefin polymers are derived include polymerizable olefin monomers characterized by the presence of one or more ethylenically unsaturated groups (i.e., $>C=C<$); that is they are monoolefinic monomers such as ethylene, propylene, 1-butene, isobutene (2-methyl-1-butene), 1-octene or polyolefinic monomers (usually diolefinic monomers), such as, 1,3-butadiene and isoprene.

The olefin monomers are usually polymerizable terminal olefins; that is, olefins characterized by the presence in their structure of the group $>C=CH_2$. However, polymerizable internal olefin monomers characterized by the presence within their structure of the group

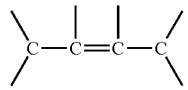

can also be used to form the polyalkenes.

Specific examples of terminal and internal olefin monomers which can be used to prepare the polyalkenes according to conventional, well-known polymerization techniques include ethylene; propylene; the butenes (butylenes), including 1-butene, 2-butene and isobutene; 1-pentene; 1-hexene; 1-heptene; 1-octene; 1-nonene; 1-decene; 2-pentene; propylene-tetramer; diisobutylene; isobutylene trimer; 1,2-butadiene; 1,3-butadiene; 1,2-pentadiene; 1,3-pentadiene; 1,4-pentadiene; isoprene; 1,5-hexadiene; 2-methyl-5-propyl-1-hexene; 3-pentene; 4-octene; and 3,3-dimethyl-1-pentene.

In one embodiment, the olefin polymer is obtained by polymerization of a $C_4$ refinery stream having a butene content of 35 to 75 weight percent and isobutene content of 30 to 60 weight percent, in the presence of a Lewis acid catalyst such as aluminum trichloride or boron trifluoride. These polybutenes typically contain predominantly (greater than 80% of total repeating units) isobutene repeating units of the configuration.

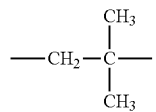

The amines that can be used include ammonia, diamines, polyamines, or mixtures thereof, including mixtures of different diamines, mixtures of different polyamines, and mixtures of diamines and polyamines. The amines include aliphatic, aromatic, heterocyclic and carbocyclic amines.

The diamines and polyamines are characterized by the presence within their structure of at least two primary amine (e.g., $H_2N$—) group. The amines can be aliphatic, cycloaliphatic, aromatic or heterocyclic.

The amine can also be a polyamine. The polyamine may be aliphatic, cycloaliphatic, heterocyclic or aromatic. Examples of the polyamines include alkylene polyamines, hydroxy containing polyamines, arylenepolyamines, and heterocyclic polyamines.

The alkylene polyamines include those represented by the formula:

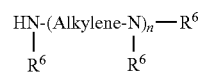

wherein n ranges from 1 to 10, and in one embodiment from 2 to 7, and in one embodiment from 2 to 5, and the "Alkylene" group has from 1 to 10 carbon atoms, and in one embodiment from 2 to 6, and in one embodiment from 2 to 4 carbon atoms. $R^5$ is independently hydrogen, aliphatic, hydroxy- or amine-substituted aliphatic group of up to 30 carbon atoms. Typically, $R^6$ is H or lower alkyl (an alkyl group of 1 to 5 carbon atoms), most typically, H. Such alkylene polyamines include ethylene polyamines, butylene polyamines, propylene polyamines, pentylene polyamines, hexylene polyamines and heptylene polyamines. The higher homologs of such amines and related aminoalkyl-substituted piperazines are also included.

Specific alkylene diamines and polyamines useful in preparing the polyalkene-substituted amines of this invention include ethylene diamine, diethylene triamine, triethylene tetramine, tetraethylene pentamine, propylene diamine, trimethylene diamine, hexamethylene diamine, decamethylene diamine, octamethylene diamine, di(heptamethylene) triamine, tripropylene tetramine, pentaethylene hexamine, di(trimethylene triamine), N-(2-aminoethyl)piperazine, and 1,4-bis(2-aminoethyl)piperazine.

Ethylene polyamines, such as those mentioned above, are especially useful for reasons of cost and effectiveness. Such polyamines are described in detail under the heading "Diamines and Higher Amines" in the Encyclopedia of Chemical Technology, Second Edition, Kirk and Othmer, Volume 7, pages 27-39, Interscience Publishers, Division of John Wiley and Sons, 1965. Such compounds are prepared most conveniently by the reaction of an alkylene chloride with ammonia or by reaction of an ethylene imine with a ring-opening reagent such as ammonia. These reactions result in the production of the somewhat complex mixtures of alkylene polyamines, including cyclic condensation products such as piperazines.

Other useful types of polyamine mixtures are those resulting from stripping of the above-described polyamine mixtures to leave as residue what is often termed "polyamine bottoms". In general, alkylenepolyamine bottoms can be characterized as having less than two, usually less than 1% (by weight) material boiling below 200° C. A typical sample of such ethylene polyamine bottoms obtained from the Dow Chemical Company of Freeport, Texas designated "E-100" has a specific gravity at 15.6° C. of 1.0168, a percent nitrogen by weight of 33.15 and a viscosity at 40° C. of 121 centistokes. Gas chromatography analysis of such a sample contains 0.93% "Light Ends" (most probably DETA), 0.72% TETA, 21.74% tetraethylene pentamine and 76.61% pentaethylenehexamine and higher (by weight). These alkylenepolyamine bottoms include cyclic condensation products such as piperazine and higher analogs of diethylenetriamine, triethylenetetramine and the like.

The hydroxy containing polyamines include hydroxyalkyl alkylene polyamines having one or more hydroxyalkyl substituents on the nitrogen atoms. Such polyamines may be made by reacting the above-described alkylenepolyamines with one or more of alkylene oxides (e.g., ethylene oxide, propylene oxide, and butylene oxide). Similar alkylene oxide-alkanolamine reaction products may also be used such as the products made by reacting primary, secondary or tertiary alkanolamines with ethylene, propylene or higher epoxides in a 1:1 to 1:2 molar ratio. Reactant ratios and temperatures for carrying out such reactions are known to those skilled in the art.

In one embodiment, hydroxyalkyl-substituted alkylene polyamines can be those in which the hydroxyalkyl group is a lower hydroxyalkyl group, i.e., having less than eight carbon atoms. Examples of such hydroxyalkyl substituted polyamines include monohydroxypropyl-substituted diethylene triamine, dihydroxypropyl-substituted tetraethylene pentamine, and N-(3-hydroxybutyl)tetramethylene diamine.

An example of an arylenepolyamine include bis-(para-aminophenyl)methane.

The number average molecular weight of the polyalkene substituted amines can range from 500 to 5000, or from 500 to 3000, and in one embodiment from 1000 to 2500.

In one embodiment, the polymer chain (Pol) is based on a Poly(alkylene). The Poly(alkylene) polymer chain may be based on a hydrocarbyl-substituted acylating agent and typically has a hydrocarbyl group with a number average molecular weight in several embodiments ranging from 300 to 5000, 450 to 4000, 500 to 3000 or 550 to 2500. In several embodiments the hydrocarbyl group has a number average molecular weight of about 550, or about 750, or 950 to 1000, or about 1600 or about 2300.

In one embodiment, the hydrocarbyl group comprises a polymer. Examples of a suitable polymer include a polyolefin.

In one embodiment, the polymer may be obtained/obtainable from at least one olefin or combinations thereof of olefins.

In several embodiments the polymer is obtained/obtainable from an olefin containing 2 to 8 carbon atoms or 3 to 6 carbon atoms. Examples of a suitable olefin include propylene, isobutylene, pentene or hexane. Typically, the polymer is derived from isobutylene to form a polyisobutylene.

In one embodiment, the polymer has a terminal C=C double bond group, i.e., a vinylidene group. Typically, the amount of vinylidene groups present is not important as a polymer (particularly polyisobutylene) may be prepared by a $BF_3$ or $AlCl_3$.

The amount of vinylidene group present is typically from at least 2 wt %, or at least 40%, or at least 50%, or at least 60%, or at least 70% of the polymer molecules. Often the amount of vinylidene group is present in about 75%, about 80% or about 85% of the molecule.

The polymer may be obtained commercially under the tradenames of Glissopal® 1000 or Glissopal® 2300 (commercially available from BASF), TPC®555, TPC®575 or TPC®595 (commercially available from Texas Petroleum Chemicals).

The acylating agent of the hydrocarbyl acylating agent may be a compound with one or more acid functional groups, such as a carboxylic acid or anhydride thereof. Examples of an acylating agent include an alpha, beta-unsaturated mono- or polycarboxylic acid, anhydride ester or derivative thereof. Examples of an acylating agent include malonic acid, succinic and phthalic acid, glutaric anhydride, succinic anhydride and phthalic anhydride, (meth) acrylic acid, methyl (meth) acrylate, maleic acid or anhydride, fumaric acid, itaconic acid or anhydride, or mixtures thereof.

INDUSTRIAL APPLICATION

The particulate solid present in the composition may be any inorganic or organic solid material which is substantially insoluble in the organic medium at the temperature concerned and which it is desired to stabilize in a finely divided form therein. The particulate solids may be in the form of a granular material, a fibre, a platelet or in the form of a powder, often a blown powder. In one embodiment, the particulate solid is a pigment.

The particulate solid (typically a pigment or filler) may have an average particle size measured by light scattering measurements of from 10 nanometers to 10 microns, or 10 nanometers to 1, 2, 3, or 5 microns, or 20 nanometers to 1, 2, 3, or 5 microns in diameter.

Examples of suitable solids are pigments for solvent inks; pigments, extenders, fillers, blowing agents and flame retardants for paints and plastic materials; dyes, especially disperse dyes; optical brightening agents and textile auxiliaries for solvent dyebaths; pigments for inks, toners and other solvent application systems; solids for oil-based and inverse-emulsion drilling muds; dirt and solid particles in dry cleaning fluids; metals; particulate ceramic materials and magnetic materials for ceramics, piezoceramic printing, refactories, abrasives, foundry, capacitors, fuel cells, ferrofluids, conductive inks, magnetic recording media, water treatment and hydrocarbon soil remediation; organic and inorganic nanodisperse solids; metal, metal oxides and carbon for electrodes in batteries, fibres such as wood, paper, glass, steel, carbon and boron for composite materials; and biocides, agrochemicals and pharmaceuticals which are applied as dispersions in organic media.

In one embodiment, the solid is an organic pigment from any of the recognised classes of pigments described, for example, in the Third Edition of the Colour Index (1971) and subsequent revisions of, and supplements thereto, under the chapter headed "Pigments". Examples of organic pigments are those from the azo, disazo, trisazo, condensed azo, azo lakes, naphthol pigments, anthanthrone, anthrapyrimidine, anthraquinone, benzimidazolone, carbazole, diketopyrrolopyrrole, flavanthrone, indigoid pigments, indanthrone, isodibenzanthrone, isoindanthrone, isoindolinone, isoindoline, isoviolanthrone, metal complex pigments, oxazine, perylene, perinone, pyranthrone, pyrazoloquinazolone, quinacridone, quinophthalone, thioindigo, triarylcarbonium pigments, triphendioxazine, xanthene and phthalocyanine series, especially copper phthalocyanine and its nuclear halogenated derivatives, and also lakes of acid, basic and mordant dyes. Carbon black, although strictly inorganic, behaves more like an organic pigment in its dispersing properties. In one embodiment, the organic pigments are phthalocyanines, especially copper phthalocyanines, monoazos, disazos, indanthrones, anthranthrones, quinacridones, diketopyrrolopyrroles, perylenes and carbon blacks.

Examples of inorganic pigments include metallic oxides such as titanium dioxide, rutile titanium dioxide and surface coated titanium dioxide, titanium oxides of different colours such as yellow and black, iron oxides of different colours such as yellow, red, brown and black, zinc oxide, zirconium oxides, aluminium oxide, oxymetallic compounds such as bismuth vanadate, cobalt aluminate, cobalt stannate, cobalt zincate, zinc chromate and mixed metal oxides of two or more of manganese, nickel, titanium, chromium, antimony, magnesium, cobalt, iron or aluminium, Prussian blue, vermillion, ultramarine, zinc phosphate, zinc sulphide, molybdates and chromates of calcium and zinc, metal effect pigments such as aluminium flake, copper, and copper/zinc alloy, pearlescent flake such as lead carbonate and bismuth oxychloride.

Inorganic solids include extenders and fillers such as ground and precipitated calcium carbonate, calcium sulphate, calcium oxide, calcium oxalate, calcium phosphate, calcium phosphonate, barium sulphate, barium carbonate, magnesium oxide, magnesium hydroxide, natural magnesium hydroxide or brucite, precipitated magnesium hydroxide, magnesium carbonate, dolomite, aluminium trihydroxide, aluminium hydroperoxide or boehmite, calcium and magnesium silicates, aluminosilicates including nanoclays, kaolin, montmorillonites including bentonites, hectorites and saponites, ball clays including natural, synthetic and expandable, mica, talc including muscovites, phlogopites, lepidolites and chlorites, chalk, synthetic and precipitated silica, fumed silica, metal fibres and powders, zinc, aluminium, glass fibres, refractory fibres, carbon black including single- and multi-walled carbon nanotubes, reinforcing and non-reinforcing carbon black, graphite, Buckminsterfullerenes, asphaltene, graphene, diamond, alumina, quartz, perlite, pegmatite, silica gel, wood flour, wood flake including soft and hard woods, saw dust, powdered paper/fibre, cellulosic fibres such as kenaf, hemp, sisal, flax, cotton, cotton linters, jute, ramie, rice husk or hulls, raffia, typha reed, coconut fibre, coir, oil palm fibre, kapok, banana leaf, caro, curaua, henequen leaf, harakeke leaf, abaca, sugar cane bagasse, straw, bamboo strips, wheat flour, MDF and the like, vermiculite, zeolites, hydrotalcites, fly ash from power plants, icinerated sewage sludge ash, pozzolanes, blast furnace slag, asbestos, chrysotile, anthophylite, crocidolite, wollastonite, attapulgite and the like, particulate ceramic materials such as alumina, zirconia, titania, ceria, silicon nitride, aluminium nitride, boron nitride, silicon carbide, boron carbide, mixed silicon-aluminium nitrides and metal titanates; particulate magnetic materials such as the magnetic oxides of transition metals, often iron and chromium, e.g., gamma-$Fe_2O_3$, $Fe_3O_4$, and cobalt-doped iron oxides, ferrites, e.g. barium ferrites; and metal particles, for instance metallic aluminium, iron, nickel, cobalt, copper, silver, gold, palladium, and platinum and alloys thereof Other useful solid materials include flame retardants such as pentabromodiphenyl ether, octabromodiphenyl ether, decabromodiphenyl ether, hexabromocyclododecane, ammonium polyphosphate, melamine, melamine cyanurate, antimony oxide and borates; biocides or industrial microbial agents such as those mentioned in tables 2, 3, 4, 5, 6, 7, 8 and 9 of the chapter entitled "Industrial Microbial Agents" in Kirk-Othmer's Encyclopedia of Chemical Technology, Volume 13, 1981, $3^{rd}$ Edition, and agrochemicals such as the fungicides flutriafen, carbendazim, chlorothalonil and mancozeb.

The organic medium present in the composition of the invention in one embodiment is a plastics material and in another embodiment an organic liquid. The organic liquid may be a non-polar or a polar organic liquid. By the term "polar" in relation to the organic liquid it is meant that an organic liquid is capable of forming moderate to strong bonds as described in the article entitled "A Three Dimensional Approach to Solubility" by Crowley et al in Journal of Paint Technology, Vol. 38, 1966, at page 269. Such organic liquids generally have a hydrogen bonding number of 5 or more as defined in the abovementioned article.

Examples of suitable polar organic liquids are amines, ethers, especially lower alkyl ethers, organic acids, esters, ketones, glycols, glycol ethers, glycol esters, alcohols and amides. Numerous specific examples of such moderately strongly hydrogen bonding liquids are given in the book entitled "Compatibility and Solubility" by Ibert Mellan (published in 1968 by Noyes Development Corporation) in Table 2.14 on pages 39-40 and these liquids all fall within the scope of the term polar organic liquid as used herein.

In one embodiment, polar organic liquids are dialkyl ketones, alkyl esters of alkane carboxylic acids and alkanols, especially such liquids containing up to, and including, a total of 6 carbon atoms. As examples of the polar organic liquids include dialkyl and cycloalkyl ketones, such as acetone, methyl ethyl ketone, diethyl ketone, di-isopropyl ketone, methyl isobutyl ketone, di-isobutyl ketone, methyl isoamyl ketone, methyl n-amyl ketone and cyclohexanone; alkyl esters such as methyl acetate, ethyl acetate, isopropyl acetate, butyl acetate, ethyl formate, methyl propionate, methoxypropyl acetate and ethyl butyrate; glycols and glycol esters and ethers, such as ethylene glycol, 2-ethoxyethanol, 3-methoxypropylpropanol, 3-ethoxypropylpropanol, 2-butoxyethyl acetate, 3-methoxypropyl acetate, 3-ethoxypropyl acetate and 2-ethoxyethyl acetate; alkanols such as methanol, ethanol, n-propanol, isopropanol, n-butanol and isobutanol (also known as 2-methylpropanol), terpineol and dialkyl and cyclic ethers such as diethyl ether and tetrahydrofuran. In one embodiment, solvents are alkanols, alkane carboxylic acids and esters of alkane carboxlic acids. In one embodiment, the present invention is suitable for organic liquids that are substantially non-soluble in an aqueous medium. Furthermore a person skilled in the art will appreciate that small quantities of an aqueous medium (such as glycols, glycol ethers, glycol esters and alcohols) may be present in the organic liquids provided the overall organic liquid is substantially non-soluble in an aqueous medium.

Examples of organic liquids, which may be used as polar organic liquids are film-forming resins such as are suitable for the preparation of inks, paints and chips for use in various applications such as paints and inks. Examples of such resins include polyamides, such as Versamid™ and Wolfamid™, and cellulose ethers, such as ethyl cellulose and ethyl hydroxyethyl cellulose, nitrocellulose and cellulose acetate butyrate resins, including mixtures thereof. Examples of paint resins include short oil alkyd/melamine-formaldehyde, polyester/melamine-formaldehyde, thermosetting acrylic/melamine-formaldehyde, long oil alkyd, medium oil alkyd, short oil alkyd, polyether polyols and multi-media resins such as acrylic and urea/aldehyde.

The organic liquid may be a polyol, that is to say, an organic liquid with two or more hydroxy groups. In one embodiment, polyols include alpha-omega diols or alpha-omega diol ethoxylates.

In one embodiment, non-polar organic liquids are compounds containing aliphatic groups, aromatic groups or mixtures thereof. The non-polar organic liquids include non-halogenated aromatic hydrocarbons (e.g. toluene and xylene), halogenated aromatic hydrocarbons (e.g. chlorobenzene, dichlorobenzene, chlorotoluene), non-halogenated aliphatic hydrocarbons (e.g. linear and branched aliphatic hydrocarbons containing six or more carbon atoms both fully and partially saturated), halogenated aliphatic hydrocarbons (e.g. dichloromethane, carbon tetrachloride, chloroform, trichloroethane) and natural non-polar organics (e.g. vegetable oil, sunflower oil, rapeseed oil, linseed oil, terpenes and glycerides).

In one embodiment, the organic liquid comprises at least 0.1% by weight, or 1% by weight or more of a polar organic liquid based on the total organic liquid. The organic liquid optionally further comprises water. In one embodiment, the organic liquid is free of water.

The plastics material may be a thermosetting resin or a thermoplastic resin. The thermosetting resins useful in this invention include resins which undergo a chemical reaction when heated, catalysed, or subject to ultra-violet, laser light, infra-red, cationic, electron beam, or microwave radiation and become relatively infusible. Typical reactions in thermosetting resins include oxidation of unsaturated double bonds, reactions involving epoxy/amine, epoxy/carbonyl, epoxy/hydroxyl, reaction of epoxy with a Lewis acid or Lewis base, polyisocyanate/hydroxy, amino resin/hydroxy moieties, free radical reactions or polyacrylate, cationic polymerization of epoxy resins and vinyl ether and condensation of silanol. Examples of unsaturated resins include polyester resins made by the reaction of one or more diacids or anhydrides with one or more diols. Such resins are commonly supplied as a mixture with a reactive monomer such as styrene or vinyltoluene and are often referred to as orthophthalic resins and isophthalic resins. Further examples include resins using dicyclopentadiene (DCPD) as a co-reactant in the polyester chain. Further examples also include the reaction products of bisphenol A diglycidyl ether with unsaturated carboxylic acids such as methacrylic acid, subsequently supplied as a solution in styrene, commonly referred to as vinyl ester resins.

In one embodiment, the thermosetting composite or thermosetting plastic may be a polyester, a polyvinyl acetate, a polyester resin in styrene, a polystyrene, or mixtures thereof.

Polymers with hydroxy functionality (frequently polyols) are widely used in thermosetting systems to crosslink with amino resins or polyisocyanates. The polyols include acrylic polyols, alkyd polyols, polyester polyols, polyether polyols and polyurethane polyols. Typical amino resins include melamine formaldehyde resins, benzoguanamine formaldehyde resins, urea formaldehyde resins and glycoluril formaldehyde resins. Polyisocyanates are resins with two or more isocyanate groups, including both monomeric aliphatic diisocyanates, monomeric aromatic diisocyanates and their polymers. Typical aliphatic diisocyanates include hexamethylene diisocyanate, isophorone diisocyanate and hydrogenated diphenylmethane diisocyanate. Typical aromatic isocyanates include toluene diisocyanates and diphenylmethane diisocyanates.

In one embodiment, thermoplastic resins include polyolefins, polyesters, polyamides, polycarbonates, polyurethanes, polystyrenics, poly(meth)acrylates, celluloses and cellulose derivatives. Said compositions may be prepared in a number of ways but melt mixing and dry solid blending are typical methods. Examples of a suitable thermoplastic include (low density, or linear low density or high density) polyethylene, polypropylene, polystyrene, polyethylene terephthalate (PET), polybutylene terephthalate (PBT), nylon 6, nylon 6/6, nylon 4/6, nylon 6/12, nylon 11 and nylon 12, polymethylmethacrylate, polyethersulphone, polysulphones, polycarbonate, polyvinyl chloride (PVC), thermoplastic polyurethane, ethylene vinyl acetate (EVA), Victrex PEEK™ polymers (such as oxy-1,4-phenylenoeoxy-1,4-phenylenecarbonyl-1,4-phenylene polymers) and acrylonitrile butadiene styrene polymers (ABS); and various other polymeric blends or alloys.

If desired, the compositions of the present invention may contain other ingredients, for example resins (where these do not already constitute the organic medium), binders, co-solvents, cross-linking agents, fluidising agents, wetting agents, anti-sedimentation agents, plasticisers, surfactants, dispersants other than the compound of the present invention, humectants, anti-foamers, anti-cratering agents, rheology modifiers, heat stabilizers, light stabilizers, UV absorbers, antioxidants, leveling agents, gloss modifiers, biocides and preservatives.

If desired, the compositions containing plastic material may contain other ingredients, for example dispersants other than the compound of the present invention, antifogging agents, nucleators, blowing agents, flame retardants, process aids, surfactants, plasticisers, heat stabilizers, UV absorbers, anti-oxidants, fragrances, mould release aids, anti-static agents, anti-microbial agents, biocides, coupling agents, lubricants (external and internal), impact modifiers, slip agents, air release agents and viscosity depressants.

The compositions typically contain from 1 to 95% by weight of the particulate solid, the precise quantity depending on the nature of the solid and the quantity depending on the nature of the solid and the relative densities of the solid and the polar organic liquid. For example, a composition in which the solid is an organic material, such as an organic pigment, in one embodiment contains from 15 to 60% by weight of the solid whereas a composition in which the solid is an inorganic material, such as an inorganic pigment, filler or extender, in one embodiment contains from 40 to 90% by weight of the solid based on the total weight of composition.

The compositions containing an organic liquid may be prepared by any of the conventional methods known for preparing dispersions. Thus, the solid, the organic medium and the dispersant may be mixed in any order, the mixture then being subjected to a mechanical treatment to reduce the particles of the solid to an appropriate size, for example by high speed mixing, ball milling, basket milling, bead milling, gravel milling, sand grinding, attritor grinding, two roll or three roll milling, plastic milling until the dispersion is formed. Alternatively, the solid may be treated to reduce its particle size independently or in admixture with either the organic medium or the dispersant, the other ingredient or ingredients then being added and the mixture being agitated to provide the composition. The composition can also be made by grinding or milling the dry solid with the dispersant and then adding the liquid medium or mixing the solid with the dispersant in a liquid medium in a pigment flushing process.

The composition containing the plastic material may be prepared by any of the conventional methods known for preparing thermoplastic compounds. Thus, the solid, the thermoplastic polymer, and the dispersant may be mixed in any order, the mixture then being subjected to a mechanical treatment to reduce the particles of the solid to an appropriate size, for example, by Banbury mixing, ribbon blending, twin-screw extrusion, twin-roll milling, compounding in a Buss co-kneader, or similar equipment.

The composition of the present invention is particularly suited to liquid dispersions. In one embodiment, such dispersion compositions comprise:
(a) from 0.5 to 80 parts of a particulate solid;
(b) from 0.1 to 79.6 parts of a polymer of formula (1); and
(c) from 19.9 to 99.4 parts of an organic liquid and/or water; wherein all relative parts are by weight and the amounts (a)+(b)+(c)=100.

In one embodiment, component a) comprises from 0.5 to 30 parts of a pigment and such dispersions are useful as (liquid) inks, paints and millbases.

If a composition is required comprising a particulate solid and a dispersant of Formula (1) in dry form, the organic liquid is typically volatile so that it may be readily removed from the particulate solid by a simple separation means such as evaporation. In one embodiment, the composition comprises the organic liquid.

If the dry composition consists essentially of the dispersant of formula (1) and the particulate solid, it typically contains at least 0.2%, at least 0.5% or at least 1.0% dispersant of formula (1) based on weight of the particulate solid. In one embodiment, the dry composition contains not greater than 100%, not greater than 50%, not greater than 20% or not greater than 10% by weight of dispersant of formula (1) based on the weight of the particulate solid.

As disclosed hereinbefore, the compositions of the invention are suitable for preparing millbases wherein the particulate solid is milled in an organic liquid in the presence of a compound for formula (1).

Thus, according to a still further aspect of the invention there is provided a millbase comprising a particulate solid, an organic liquid and a polymer of formula (1).

Typically, the millbase contains from 20 to 70% by weight particulate solid based on the total weight of the millbase. In one embodiment, the particulate solid is not less than 10 or not less than 20% by weight of the millbase. Such millbases may optionally contain a binder added either before or after milling.

In one embodiment, the binder is a polymeric material capable of binding the composition on volatilisation of the organic liquid.

Binders are polymeric materials including natural and synthetic materials. In one embodiment, binders include poly(meth)acrylates, polystyrenics, polyesters, polyurethanes, alkyds, polysaccharides such as cellulose, nitrocellulose, and natural proteins such as casein. The binder may be nitrocellulose. In one embodiment, the binder is present in the composition at more than 100% based on the amount of particulate solid, more than 200%, more than 300% or more than 400%.

The amount of optional binder in the millbase can vary over wide limits but is typically not less than 10%, and often not less than 20% by weight of the continuous/liquid phase of the millbase. In one embodiment, the amount of binder is not greater than 50% or not greater than 40% by weight of the continuous/liquid phase of the millbase.

The amount of dispersant in the millbase is dependent on the amount of particulate solid but is typically from 0.5 to 5% by weight of the millbase.

Dispersions and millbases made from the composition of the invention are particularly suitable for use in non-aqueous and solvent free formulations in which energy curable systems (ultra-violet, laser light, infra-red, cationic, electron beam, microwave) are employed with monomers, oligomers, etc or a combination present in the formulation. They are particularly suitable for use in coatings such as paints, varnishes, inks, other coating materials and plastics. Suitable examples include their use in low, medium and high solids paints, general industrial paints including baking, two component and metal coating paints such as coil and can coatings, powder coatings, UV-curable coatings, wood varnishes; inks, such as flexographic, gravure, offset, lithographic, letterpress or relief, screen printing and printing inks for packaging printing, non impact inks such as inkjet inks including continuous inkjet and drop on demand inkjet which include thermal, piezo and electrostatic, phase change inks and hot melt wax inks, inks for ink jet printers and print varnishes such as overprint varnishes; polyol and plastisol dispersions; non-aqueous ceramic processes, especially tape-casting, gel-casting, doctor-blade, extrusion and injection moulding type processes, a further example would be in the preparation of dry ceramic powders for isostatic pressing; composites such as sheet moulding and bulk moulding compounds, resin transfer moulding, pultrusion, hand-lay-up and spray-lay-up processes, matched die moulding; construction materials like casting resins, cosmetics, personal care like nail coatings, sunscreens, adhesives, toners such as liquid toners, plastics materials and electronic materials such as coating formulations for colour filter systems in displays including organic light-emitting diode (OLED) devices, liquid crystal displays and electrophoretic displays, glass coatings including optical fibre coatings, reflective coatings or anti-reflective coatings, conductive and magnetic inks and coatings. They are useful in the surface modification of pigments and fillers to improve the dispersibility of dry powders used in the above applications. Further examples of coating materials are given in Bodo Muller, Ulrich Poth, Lackformulierung und Lackrezeptur, Lehrbuch fr Ausbildung und Praxis, Vincentz Verlag, Hanover (2003) and in P. G. Garrat, Strahlenhartung, Vincentz Verlag, Hanover (1996). Examples of printing ink formulations are given in E. W. Flick, Printing Ink and Overprint Varnish Formulations—Recent Developments, Noyes Publications, Park Ridge N.J., (1990) and subsequent editions In one embodiment, the composition of the invention further includes one or more additional known dispersants.

The following examples provide illustrations of the invention. These examples are non-exhaustive and are not intended to limit the scope of the invention.

EXAMPLES

Comparative Example 1 (CE1)

1,2,4-Benzene tricarboxylic anhydride (17.03 parts) is added to a stirred polyether amine (consisting of C12-15 alcohol reacted with propylene oxide (MW 1800), followed by base catalysed addition of the resultant polyether alcohol to acrylonitrile and subsequent hydrogenation to give an amine (85% active) (200 parts). The IR is consistent with imide formation and the final product has an acid value 26.97 mgKOH/g. The product is similar to a dispersant prepared according to PREP2 in International publication WO2008/028954.

Comparative Example 2 (CE2)

1,8 Naphthalic anhydride (14.46 parts) is added to a stirrer polyether amine (150 parts Surfonamine L207 ex Huntsman). The reaction is stirred at 100° C. under nitrogen for 8 hours then 150° C. for 12 hours. The IR is consistent with imide formation and the final product has an acid value 5.46 mgKOH/g. The product is similar to a dispersant prepared according to the disclosure in U.S. Pat. No. 6,440,207.

Example 1

3-Nitro-1,8-naphthalic anhydride (2.91 parts) is added to a stirred polyetheramine (27.09 parts, Surfonamine B200 ex Huntsman). The reaction is stirred at 170° C. under nitrogen for 5 hours. The IR is consistent with imide formation and the final product has an acid value of 1.19 mgKOH/g.

Example 2

4-Nitro-1,8-naphthalic anhydride (4.82 parts) is added to a stirred polyetheramine (44.80 parts, Surfonamine B200 ex Huntsman). The reaction is stirred at 170° C. under nitrogen for 5 hours. The IR is consistent with imide formation and the final product has an acid value 0.75 mgKOH/g.

Example 3

4-Chloro-1,8-naphthalic anhydride (4.17 parts) is added to a stirred polyetheramine (35.83 parts, Surfonamine B200 ex Huntsman). The reaction is stirred at 170° C. under nitrogen for 25 hours. The IR is consistent with imide formation and the final product has an acid value 1.24 mgKOH/g.

Example 4

1,8-Naphthalic anhydride (17.75 parts) is added to a stirred polyether amine (consisting of C12-15 alcohol reacted with propylene oxide (MW 1800), followed by base catalysed addition of the resultant polyether alcohol to acrylonitrile and subsequent hydrogenation to give an amine (85% active) (200 parts). The reaction is stirred at 170° C. under nitrogen for 5 hours. The IR is consistent with imide formation and the final product has an acid value 4.12 mg KOH/g.

Example 5

1,2-Naphthalic anhydride (1.98 parts) is added to a stirred polyether amine (consisting of C12-15 alcohol reacted with propylene oxide (MW 1800), followed by base catalysed addition of the resultant polyether alcohol to acrylonitrile and subsequent hydrogenation to give an amine (85% active) (23.0 parts). The reaction is stirred at 100° C. for 1 hour then is stirred at 175° C. for 2 hours under nitrogen. The IR is consistent with imide formation and the final product acid value is 2.10 mgKOH/g.

Dispersion Test 1

A dispersion was prepared by dissolving examples 1-5 and CE1 and CE2 (0.5 parts) in ethanol/ethyl acetate (6.0 parts, 5:1 w/w). Nitrocellulose resin (1.0 parts, NC-DLX 3/5 (ex Nobel NC), 20% solids in ethanol/ethyl acetate 5:1) is then added followed by 3 mm glass beads (25 parts) and black pigment (Printex®35 ex Degussa, 2.5 parts). The contents were milled on a horizontal shaker for 16 hours. The dispersion is coated onto black and white card and after evaporation of solvent the gloss was measured using a Novogloss meter ex Rhopoint instruments. Typically, better results are obtained for examples with a higher 60° C. Gloss rating. The results obtained for each dispersion are:

| Example | 60° C. Gloss |
|---------|--------------|
| CE1 | 16 |
| CE2 | 8 |
| 1 | 106 |
| 2 | 70 |
| 3 | 53 |
| 4 | 99 |
| 5 | 87 |

Intermediate A:
2-(2-aminoethoxyl)ethanol (15.92 parts) is added to 1,8 Naphthalic anhydride (30.00 parts) and is stirred under nitrogen for 9 hours at 160° C. The IR is consistent with imide formation and the final product acid value is 4.83 mgKOH/g.

Intermediate B:
2-(2-aminoethoxyl)ethanol (30.27 parts) is added to 3-Nitro 1,8 Naphthalic Anhydride (70.00 parts) and is stirred under nitrogen for 6 hours at 180° C. The IR is consistent with imide formation and the final product acid value is 2.07 mgKOH/g.

Intermediate C:
Ethylene oxide (122.72 parts) is added to Intermediate A (99.35 parts) and potassium hydroxide (1.0 parts) and is stirred under nitrogen for 4 hours at 155° C. The resulting product is a brown liquid and the molecular weight is Mn=414 and Mw=519 as determined by GPC (THF eluent, PEG Standards).

Intermediate D:
Ethylene diamine (20 parts) is dissolved in water (80 parts) and a suspension of 1,8 Naphthalic anhydride (10 parts) in water (60 parts) is added over 20 minutes. The mixture is heated to 70° C. for 45 minutes then filtered to remove impurities. The resulting solution is cooled to 5° C. and the product is precipitated as a yellow solid and the IR is consistent with imide formation.

Intermediate E:
1,8 naphthalic anhydride (10 parts) is added to sulphuric acid, (30 parts 30% as free $SO_3$ and 30 parts 20% as free $SO_3$) over 25 minutes at 0° C. The mixture is heated to 95° C. for 1 hour then poured over iced water (70 parts). The resulting precipitate is filtered and washed with glacial acetic acid (40 parts), hexane (40 parts) and hydrochloric acid (40 parts) then dried. The resulting product contained 10.3% sulphur and the NMR is consistent with sulfonation.

Intermediate F:
The same procedure and amounts as outlined in Preparation 2 of U.S. Pat. No. 6,403,797 is used except that naphthalic anhydride is replaced with 3-Nitronaphthalic anhydride (30.6 parts). A beige solid (35.4 parts) is obtained and the NMR is consistent with the required product and the final product acid value is 18.9 mgKOH/g.

Example 6

3-Nitro-1,8-Napthalic anhydride (21.56 parts) is added to a stirred polyether amine (consisting of C12-15 alcohol reacted with propylene oxide (MW 1800), followed by base catalysed addition of the resultant polyether alcohol to acrylonitrile and subsequent hydrogenation to give an amine (85% active) (200 parts). The reaction is stirred at 160° C. under nitrogen for 4 hours. The IR is consistent with imide formation and the final product acid value is 4.93 mgKOH/g.

Example 7

1,8 Naphthalic Anhydride (18.22 parts) is added to a stirred polyetheramine (46.02 parts, Surfonamine B200 ex Huntsman). The reaction is stirred at 175° C. for 4 hours under nitrogen. The IR is consistent with imide formation and the final product acid value is 4.47 mgKOH/g.

Example 8

1,2 Naphthalic Anhydride (3.98 parts) is added to a stirred polyetheramine (46.02 parts, Surfonamine B200 ex Huntsman). The reaction is stirred at 100° C. for 1 hour under nitrogen then is heated to 175° C. under nitrogen for 5 hours. The IR is consistent with imide formation and the final product acid value is 4.31 mgKOH/g.

Example 9

2,3 Napthalic anhydride (7.96 parts) is added to a stirred polyetheramine (92.05 parts, Surfonamine B200 ex Huntsman). The reaction is stirred at 100° C. for 1 hour under nitrogen then is heated to 175° C. under nitrogen for 5 hours. The IR is consistent with imide formation and the final product acid value is 1.39 mgKOH/g.

Example 10

Propylene oxide (214.54 parts) is added to Intermediate C (98.15 parts) and potassium hydroxide (0.7 parts) and is stirred under nitrogen at 155° C. for 24 hours. The resulting product is a brown liquid the molecular weight is Mn=1390 and Mw=1956 as determined by gel permeation chromatography (GPC) (tetrahydrofuran (THF) eluent, polyethylene glycol (PEG) Standards).

Example 11

3-Nitro 1,8 Naphthalic Anhydride (38.69 parts) is added to a stirred polyetheramine (161.32 parts, Surfonamine B100 ex Huntsman). The reaction is stirred at 100° C. for 1 hour under nitrogen then heated to 175° C. under nitrogen for 2 hours. The IR is consistent with imide formation and the final product acid value is less than 1.0 mgKOH/g.

Example 12

3-Nitro 1,8 Naphthalic Anhydride (26.74 parts) is added to a stirred polyetheramine (73.26 parts, Surfonamine B60 ex Huntsman). The reaction is stirred at 100° C. for 1 hour under nitrogen then is heated to 175° C. under nitrogen for 4 hours. The IR is consistent with imide formation and the final product acid value is 2.46 mgKOH/g.

Example 13

Triethylamine (1.09 parts) is added to a stirred solution of Intermediate E (2.93 parts) dissolved in acetone (50 parts). The reaction mixture is stirred under nitrogen for 30 minutes at room temperature, then polyether amine (consisting of C12-15 alcohol reacted with propylene oxide (MW 1800), followed by base catalysed addition of the resultant polyether alcohol to acrylonitrile and subsequent hydrogenation to give an amine (85% active) (25.97 parts) is added. The reaction mixture is stirred at 70° C. for 1 hour remove the acetone by distillation. The mixture is then heated to 100° C. for 1 hour and 175° C. for 5 hours. The IR is consistent with imide formation and the final product acid value is 23.9 mgKOH/g.

Example 14

Intermediate A (10.00 parts), ε-caprolactone (31.30 g) and delta-valerolactone (35.70 g) is stirred under nitrogen at 90° C., zirconium (IV) butoxide (0.23 g) is added and the mixture is heated to 180° C. for 6 hours. The resulting product is a dark brown liquid and molecular weight is Mn=1300 and Mw=1800 as determined by GPC (THF eluent, polystyrene Standards).

Example 15

Intermediate B (3.28 parts), ε-caprolactone (9.61 parts) and delta-valerolactone (10.96 parts) is stirred under nitrogen at 90° C., zirconium (IV) butoxide (0.07 parts) is added and the mixture heated to 180° C. for 6 hours. The resulting product is a dark brown liquid and molecular weight is Mn=1320 and Mw=1800 as determined by GPC (THF eluent, polystyrene standards).

Example 16

Intermediate A (5.6 parts), Epsilon-Caprolactone (84.11 parts) is stirred under nitrogen at 90° C., zirconium (IV) butoxide (0.24 parts) is added the mixture heated to 180° C. for 6 hours. The resulting product is a dark brown liquid and molecular weight is Mn=1800 and Mw=2200 as determined by GPC (THF eluent, polystyrene standards).

Example 17

Intermediate B (2.0 parts), Epsilon-Caprolactone (11.72 parts) is stirred under nitrogen at 90° C., zirconium (IV) butoxide (0.04 parts) is added and the mixture heated to 180° C. for 6 hours. The resulting product is a dark brown liquid and molecular weight is Mn=1300 and Mw=1700 as determined by GPC (THF eluent, polystyrene standards).

Example 18

Intermediate C (10.86 parts) and epsilon caprolactone (20 parts) are stirred under nitrogen at 90° C. Ortho-phosphoric acid (0.1 g) is added and the reaction mixture heated to 120° C. for 6 hours. The resulting product is a waxy solid and with molecular weight Mn=1183 and Mw=1586 as determined by GPC (THF eluent, polycaprolactone standards).

Example 19

Intermediate A (5.02 parts), ricinoleic acid (10.49 parts) epsilon caprolactone (9.25 parts) and delta valerolactone (5.98 parts) is stirred under nitrogen at 120° C., zirconium (IV) butoxide (0.08 parts) is added and the mixture heated to 180° C. for 48 hours. The resulting product is a waxy solid with molecular weight Mn=1268 and Mw=1826 as determined by GPC (THF eluent, polystyrene standards).

Example 20

Intermediate A (4.74 parts), 12-hydroxysteric acid (25.03 parts) is stirred under nitrogen at 120° C., zirconium (IV) butoxide (0.09 parts) is added and the mixture heated to 180° C. for 48 hours. The resulting product is a waxy solid with molecular weight Mn=1791 and Mw=2149 as determined by GPC (THF eluent, polystyrene standards).

Example 21

Intermediate A (5.16 parts), 12-hydroxysteric acid (16.32 parts) and epsilon caprolactone (6.19 parts) is stirred under nitrogen at 120° C., zirconium (IV) butoxide (0.08 parts) is added and the mixture heated to 180° C. for 26 hours. The resulting product is a waxy solid with molecular weight

41

Mn=1429 and Mw=1766 as determined by GPC (THF eluent, polystyrene standards).

Example 22

1,8 Naphthalic anhydride (18.57 parts) is added to a stirred poly(isobutylene) amine (152.99 parts, Mn=1100, 65% in mineral oil). The reaction is stirred at 100° C. for 2 hours under nitrogen is heated to 170° C. for 6 hours. The IR is consistent with imide formation and the final product acid value is 0.5 mgKOH/g.

Example 23

3-Nitro-1,8 Naphthalic anhydride (25.99 parts) is added to a stirred poly(isobutylene) amine (174.45 parts, Mn=1100, 65% in mineral oil). The reaction is stirred at 100° C. for 2 hours under nitrogen and then heated to 170° C. for 13 hours. The IR is consistent with imide formation and the final product acid value is 0.9 mgKOH/g.

Example 24

Intermediate D (5.0 parts) is added to a stirred poly(isobutylene)succininc anhydride (16.61 parts, Mn 750). The reaction is stirred at 120° C. for 1 hours under nitrogen then heated to 180° C. for 33 hours. The IR is consistent with imide formation and the final product acid value is 6.0 mgKOH/g.

Example 25

Intermediate F (4.0 parts) is added to stirred caprolactone (19.77 parts). The reaction is stirred at 120° C. under nitrogen and then zirconium butoxide (80% in 1-butanol) (0.2 parts) is added. The reaction mixture is heated to 180° C. for 8 hours. The final product acid value is 32.4 mgKOH/g.

Example 26

3-Nitronaphthalic anhydride (10.0 parts) is added portionwise to stirred 12-aminododecanoic acid (35.4 parts) at 190° C. over 1 hour under nitrogen. IR is consistent with imide formation. Caprolactone (32.86 parts) is slowly added to the mixture via an addition funnel and finally methanesulphonic acid (0.2 parts) and then the mixture is heated at 180° C. for 16 hours. The final product acid value is 31.9 mgKOH/g.

Dispersion Test 2

Examples 4, 6, and 7 and CE1 (0.5 parts) and polyamide resin (0.5 parts, Unirez™ 138 ex Arizona Chemicals) are dissolved in isopropyl alcohol/butyl acetate (7.0 parts, 7:3 w/w). 3 mm glass beads (25 parts) and black pigment (Printex®35 ex Degussa, 2.0 parts) are added and the contents milled on a horizontal shaker for 16 hours. The resulting millbase (0.5 parts) is then added to polyamide resin (0.5 parts, Unirez 138™ 138 ex Arizona Chemicals) and drawn down onto black and white card with a number 2-K bar. After evaporation of the solvent, the gloss is measured using a Novogloss meter ex Rhopoint instruments. The results obtained are as follows:

| Example | Gloss 60° C. |
|---|---|
| CE1 | 19 |
| 4 | 78 |

-continued

| Example | Gloss 60° C. |
|---|---|
| 6 | 83 |
| 7 | 74 |

Dispersion Test 3

Examples 7-12 and CE1 (0.6 parts) and polyurethane resin (1.0 parts, Neorez™ U-471, ex DSM Neoresins, 51% active in ethanol:ethyl acetate 2/1 w/w) are dissolved in isopropyl alcohol/butyl acetate (7.4 parts, 7:3 w/w). 3 mm glass beads (17 parts) and black pigment (Printex 35 ex Degussa, 1.0 parts) are added and the contents milled on a horizontal shaker for 16 hours. The resulting fluid millbase (0.5 parts) is then added to polyurethane resin (1.0 parts, Neorez U-471 ex DSM Neoresins, 34% active in ethanol:ethyl acetate 2/1 w/w) and drawn down onto black and white card with a number 3-K bar. After evaporation of the solvent, the gloss is measured using a Novogloss meter ex Rhopoint instruments. The results obtained are as follows:

| Example | Gloss 60° C. |
|---|---|
| CE1 | 32 |
| 7 | 57 |
| 8 | 56 |
| 9 | 56 |
| 10 | 78 |
| 11 | 68 |
| 12 | 72 |
| 13 | 77 |

Dispersion Test 4

A dispersion is prepared by dissolving examples 13-16 (0.6 parts) in a mixture of methoxypropyl acetate (1.6 parts) and butyl acetate (4.8 parts). Acrylic resin (2.0 parts, Doresco®TA96-6 ex Lubrizol) is then added followed by 3 mm glass beads (17 parts) and black pigment (1.0 parts FW200, ex Degussa) and the contents milled on a horizontal shaker for 16 hours. All the resulting dispersions are all fluid. The dispersions (0.5 parts) are let down into acrylic resin (1.5 parts, Doresco TA96-9 ex Lubrizol) and drawn down onto black and white card using a No 3 K bar. The coatings are assessed visually to determine the extent of shock seeding.

| Coating with Example | Gloss 60° | Shock seeding |
|---|---|---|
| 14 | 90 | no |
| 15 | 91 | no |
| 16 | 90 | no |
| 17 | 89 | no |

Dispersion Test 5

A dispersion is prepared by dissolving examples 19, 20, 21, 22 and CE1 (based on 1.0 parts, 100% active) in solvent (7.0 parts), 3 mm glass beads (17 parts) and red pigment (2.0 parts, Cromophtal® red A2B, ex Ciba) are then added and the contents milled on a horizontal shaker for 16 hours. The viscosity was assessed by determining the freedom of the glass beads to move throughout the millbase. In all cases except CE1 the pigment wetted out and a homogeneous dispersion is formed. The results from dispersion test 5 are:

| Example | Solvent | Viscosity |
| --- | --- | --- |
| CE1 | toluene | gelled |
| CE1 | Butyl acetate | gelled |
| CE1 | 2 Ethanol:1Ethyl acetate | gelled |
| 18 | 2 Ethanol:1Ethyl acetate | fluid |
| 19 | butyl acetate | fluid |
| 20 | toluene | fluid |
| 21 | toluene | fluid |
| 22 | toluene | fluid |
| 23 | toluene | fluid |
| 24 | toluene | fluid |
| 25 | toluene | fluid |
| 26 | toluene | fluid |

Overall, the results presented above indicate that the polymers of the invention provide at least one of improving colour strength, increasing a particulate solid load, forming improved dispersions, having improved brightness, and producing a composition with reduced viscosity in an organic medium.

The terms "hydrocarbyl" or "hydrocarbylene" denotes a group having a carbon atom directly attached to the remainder of the molecule and having a hydrocarbon or predominantly hydrocarbon character within the context of this invention. Such groups include the following: (1) Purely hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc. (2) Substituted hydrocarbon groups; that is, groups containing non-hydrocarbon substituents which do not alter the predominantly hydrocarbon character of the group. Those skilled in the art will be aware of suitable substituents. Examples include hydroxy, nitro, cyano, alkoxy, acyl, etc. (3) Hetero groups; that is, groups which, while predominantly hydrocarbon in character, contain atoms other than carbon in a chain or ring otherwise composed of carbon atoms. Suitable hetero atoms will be apparent to those skilled in the art and include, for example, nitrogen, oxygen and sulphur.

As described hereinafter the number average molecular weight of the polymer of the present invention has been determined using known methods, such as GPC analysis using a polystyrene standard for all polymer chains except those that contain ethylene oxide. The number average molecular weight of a polymer chain containing ethylene oxide is determined by GPC (THF eluent, PEG Standards).

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

As used herein the term "hydrocarbylene" is used in the ordinary sense of the term and is intended to include any divalent radical formed by removing two hydrogen atoms from a hydrocarbon.

As used herein the term "alk(en)ylene" is used in the ordinary sense of the term and is intended to include an alkylene and/or an alkenylene group.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A polymer comprising a polymer chain having at least one fused aromatic imide pendant group, wherein the polymer is represented by formula (1):

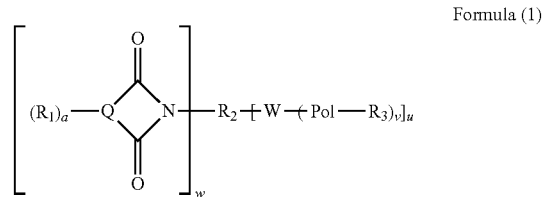

Formula (1)

wherein each variable is independently $R_1$ is a substituent on Q ring in any position available for bonding to a substituent group and $R_1$ is represented by one or more of —H, or an electron withdrawing group chosen from a halogen, a nitrile, a nitro group, a sulphamoyl group, a sulphonate group, a hydroxy group, or an amino group;

$R_2$ is a $C_1$ to $C_{20}$ hydrocarbylene group or a $C_1$ to $C_{20}$ hydrocarbonylene group when $R_2$ contains more than 2 carbon atoms, the hydrocarbylene group or hydrocarbonylene group is linear or branched or mixtures thereof;

$R_3$ is a H or $C_{1-50}$-optionally substituted hydrocarbyl group that bonds to a terminal oxygen atom of the polymer chain forming a terminal ether or terminal ester group and may or may not contain a group capable of polymerization such as a vinyl group, or $C_{1-50}$-hydrocarbonyl group that bonds to the oxygen atom of the polymer chain forming a terminal ester group or terminal urethane group and may or may not contain a group capable of polymerization;

Pol is a homopolymer chain or a copolymer chain, wherein the polymer chain is selected from the group consisting essentially of a Poly(ether); of the structure $(CH_2—CH(R_4)—O—)_m$ and $R_4$ is methyl, ethyl or phenyl when Pol is a homopolymer, and $R_4$ is a mixture of H in an amount sufficient to provide ethylene oxide groups at 0 wt % to 60 wt % and at least one of methyl, ethyl and phenyl or mixtures thereof;

u is 1 to 3;

v is 1 to 2;

w is 1 to 3;

m is 1 to 110;

v is 2 when W is Nitrogen;

v is 1 when W is Oxygen, Sulphur, or >NG;

G is a hydrogen or a hydrocarbyl group containing 1 to 200 carbon atoms

Q is a fused aromatic naphthalene ring and

Q is bonded to the imide group in such a way to form a 5 or 6 membered imide ring.

2. The polymer of claim 1 which is obtained by a process comprising:

Step (1): reacting (i) amino acid or (ii) an aminoalcohol, or (iii) an aminothiol, or (iv) a diamine or polyamine, with a fused aromatic naphthalene di-acid or anhydride to form an acid-functionalised fused aromatic naphthalene imide or an hydroxyl-functionalised fused aromatic naphthalene imide, or a thiol-functionalised fused aromatic naphthalene imide, or an amino-functionalised fused aromatic naphthalene imide respectively;

Step (2): reacting the acid-functionalised fused aromatic naphthalene imide or the hydroxyl-functionalised fused aromatic naphthalene imide, or the thiol-functionalised fused aromatic naphthalene imide, or the amino-functionalised fused aromatic naphthalene imide with a polyether chain, or monomers that polymerise to form the polyether chain.

3. The polymer of claim 1, which is obtained by a process comprising:

reacting a polyether amine with a naphthalene diacid or anhydride to form the product.

4. The polymer of claim 1, wherein the polymer chain is a poly(ether) represented by Formula (2):

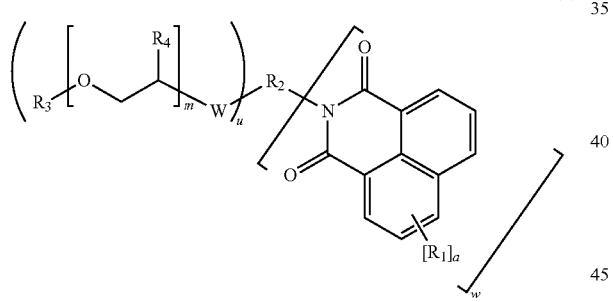

Formula (2)

wherein each variable is independently $R_1$ is a substituent in any position and $R_1$ is represented by one or more of —H, or an electron withdrawing group chosen from a halogen, a nitrile, a nitro group, a sulphamoyl group, a sulphonate group, a hydroxy group, or an amino group;

W is oxygen;

$R_2$ is a $C_1$ to $C_{20}$ hydrocarbylene group or a $C_1$ to $C_{20}$ hydrocarbonylene group when $R_2$ contains more than 2 carbon atoms, the hydrocarbylene group or hydrocarbonylene group is linear or branched or mixtures thereof;

$R_3$ is a H or $C_{1-50}$-optionally substituted hydrocarbyl group that bonds to a terminal oxygen atom of the polymer chain forming a terminal ether or terminal ester group and may or may not contain a group capable of polymerization such as a vinyl group, or $C_{1-50}$-hydrocarbonyl group that bonds to the oxygen atom of the polymer chain forming a terminal ester group or terminal urethane group and may or may not contain a group capable of polymerization such as a vinyl group, and the substituent is halo, ether, ester, or mixtures thereof;

$R_4$ is methyl, ethyl or phenyl when Pol is a homopolymer, and $R_4$ is a mixture of H in an amount sufficient to provide ethylene oxide groups at 0 wt % to 60 wt % and at least one of methyl, ethyl and phenyl or mixtures thereof;

u is 1 to 3;

w is 1 to 3;

with the proviso that when $R_2$ is a hydrocarbylene group, u is 1 and w is 1; and m is 1 to 110.

5. The polymer of claim 1, wherein the polymer chain is a poly(ether) polymer chain represented by Formula (3a):

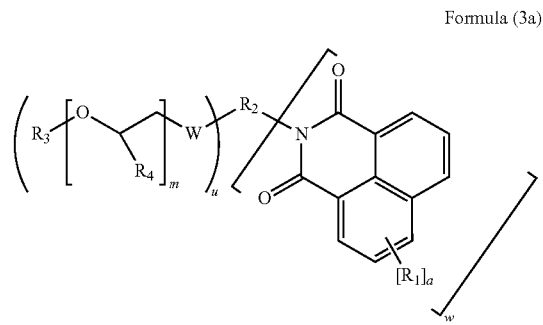

Formula (3a)

wherein each variable is independently $R_1$ is a substituent in any position and $R_1$ is represented by one or more of —H, or an electron withdrawing group chosen from a halogen, a nitrile, a nitro group, a sulphamoyl group, a sulphonate group, a hydroxy group, or an amino group;

W is sulphur, oxygen or >NG;

$R_2$ is a $C_1$ to $C_{20}$ hydrocarbylene group or a $C_1$ to $C_{20}$ hydrocarbonylene group when $R_2$ contains more than 2 carbon atoms, the hydrocarbylene group or hydrocarbonylene group is linear or branched or mixtures thereof;

G is a hydrocarbyl group containing 1 to 200 carbon atoms;

$R_3$ is a H or $C_{1-50}$-optionally substituted hydrocarbyl group that bonds to a terminal oxygen atom of the polymer chain forming a terminal ether or terminal ester group and may or may not contain a group capable of polymerization such as a vinyl group, or $C_{1-50}$-hydrocarbonyl group that bonds to the oxygen atom of the polymer chain forming a terminal ester group or terminal urethane group and may or may not contain a group capable of polymerization such as a vinyl group, and the substituent is halo, ether, ester, or mixtures thereof;

$R_4$ is methyl, ethyl or phenyl when said polyether is a homopolymer, and $R_4$ is a mixture of H in an amount sufficient to provide ethylene oxide groups at 0 wt % to 60 wt and at least one of methyl, ethyl and phenyl or mixtures thereof;

u is 1 to 3;

w is 1 to 3; and m is 1 to 110.

6. The polymer of claim 1, wherein the polymer chain is a poly(ether) polymer chain represented by Formula (3b):

Formula (3b)

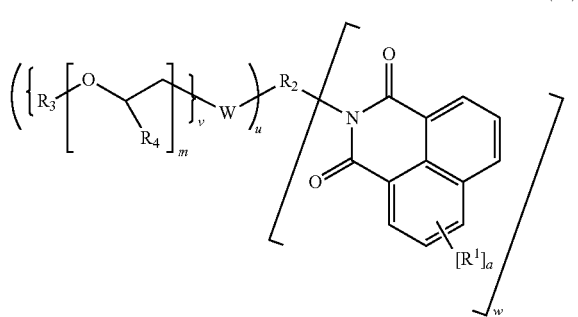

wherein each variable is independently $R_1$ is a substituent in any position and $R_1$ is independently represented by one or more of an electron withdrawing group chosen from a halogen, a nitrile, a nitro group, a sulphamoyl group, a sulphonate group, a hydroxy group, or an amino group;

W is nitrogen;

$R_2$ is a $C_1$ to $C_{20}$ hydrocarbylene group or a $C_1$ to $C_{20}$ hydrocarbonylene group when $R_2$ contains more than 2 carbon atoms, the hydrocarbylene group or hydrocarbonylene group is linear or branched or mixtures thereof;

$R_3$ is H or $C_{1-50}$-hydrocarbonyl group that bonds to the oxygen atom of the polymer chain forming a terminal ester group or terminal urethane group and may or may not contain a group capable of polymerization such as a vinyl group, and the substituent is halo, ether, ester, or mixtures thereof;

$R_4$ is methyl, ethyl or phenyl when said polyether is a homopolymer, and $R_4$ is a mixture of H (in an amount sufficient to provide ethylene oxide groups at 0 wt % to 60 wt %) and at least one of methyl, ethyl and phenyl, or mixtures thereof;

u is 1 to 3;

w is 1 to 3;

v is 2; and m is 1 to 110.

7. A composition comprising a particulate solid, a non-polar organic medium, and a polymer chain having at least one fused aromatic imide pendant group, wherein the polymer is represented by a polymer claim 1.

8. A composition comprising a particulate solid, a polar organic medium, and a polymer chain having at least one fused aromatic imide pendant group, wherein the polymer is represented by a polymer of claim 1.

9. The composition of claim 8, wherein the composition is a millbase, paint or ink.

10. The composition of claim 8, wherein the particulate solid is a pigment or a filler.

11. A composition comprising a polymer chain having at least one fused aromatic imide pendant group, wherein the polymer is represented by claim 1, a particulate solid (typically a pigment or filler), and either (i) a polar organic medium or (ii) a non-polar organic medium, wherein the organic medium is a plastic material.

12. The composition of claim 8, wherein the polymer is present in an amount ranging from 0.5 wt % to 30 wt % of the composition.

13. The composition of claim 8, wherein the polymer is present in an amount ranging from 1 wt % to 25 wt % of the composition.

* * * * *